(12) United States Patent
Agur et al.

(10) Patent No.: US 7,418,374 B2
(45) Date of Patent: Aug. 26, 2008

(54) TREATMENT PROTOCOL GENERATION FOR DISEASES RELATED TO ANGIOGENESIS

(75) Inventors: Zvia Agur, Tel Aviv (IL); Levon Arakelyan, Ashdod (IL); Vladimir Vainstein, Jerusalem (IL)

(73) Assignee: OPTIMATA, Tel Aviv (IL)

( * ) Notice: Subject to any disclaimer, the term of this patent is extended or adjusted under 35 U.S.C. 154(b) by 0 days.

(21) Appl. No.: 10/207,772

(22) Filed: Jul. 31, 2002

(65) Prior Publication Data

US 2003/0088237 A1    May 8, 2003

Related U.S. Application Data

(60) Provisional application No. 60/330,592, filed on Oct. 25, 2001.

(51) Int. Cl.
*G06N 3/00* (2006.01)

(52) U.S. Cl. .................. 703/11; 702/19; 703/2

(58) Field of Classification Search ............ 702/19; 703/11, 12
See application file for complete search history.

(56) References Cited

OTHER PUBLICATIONS

Guidi et al. Database CaPlus, DN:136:318985. Journal of Clinical Oncology (2002), 20(3), 732-742.*
Hahnfeldt P. et al. (1999) Tumor development under angiogenic signaling: a dynamic theory of tumor growth, treatment response, and postvascular dormancy. Cancer Res. 59:4770-4775.*
Anderson AR and Chaplain MA (1998) Continuous and discrete mathematical models of tumor-induced angiogenesis. Bull Math Biol. 604(5):857-99.*
Tong S and Yuan F (2001) Numelical simulations of angiogenesis in the cornea. Microvasc Res; 6141): 14-27.*
Augustin et al. American Journal of Pathology, 147 (2), 339-351, 1995.*
Anderson et al Bulletin of Mathematical Biology, 60, 857-900, 1998.*
Lissbrant et al . Prostate, 33:38-45, 1997.*
Folkman, J., Angiogenesis in cancer, vascular, rheumatoid and other disease, Nat Med., 1995, pp. 27-31, vol. 1(1).
Carmeliet, P. et al, Angiogenesis in cancer and other diseases, Nature, 2000, pp. 249-257, vol. 407.
Yancopoulos, G.D. et al, Vascular-specific growth factors and blood vessel formation, Nature, 2000, pp. 242-248, vol. 407.
Kerbel, R.S., Tumor angiogenesis: past, present and the near future, Carcinogenesis, 2000, pp. 505-515, vol. 21(3).
Danielsen, T et al, The constitutive level of vascular endothelial growth factor (VEGF) is more important than hypoxia-induced VEGF up-regulation in the angiogenesis of human melanoma xenografts, Br. J. Can., 2000, pp. 1528-1534, vol. 82(9).

(Continued)

*Primary Examiner*—Michael Borin
(74) *Attorney, Agent, or Firm*—Sughrue Mion, PLLC

(57) ABSTRACT

A computer-implemented method for determining an optimal treatment protocol for a disease related to angiogenesis, comprising creating an angiogenesis model including pro-angiogenic and anti-angiogenic factors. Effective vessel density (EVD) is incorporated as a factor regulating switching on and switching off of at least one component in the angiogenesis model. Effects of vasculature maturation and mature vessel destabilization are incorporated. Pro-angiogenic and anti-angiogenic factors, which can influence changes in state of a tissue, are selected. Effects of drugs in the pro-angiogenic and anti-angiogenic factors are incorporated. A plurality of treatment protocols in a protocol space is generated. A best treatment protocol based on a pre-determined criteria is selected.

40 Claims, 13 Drawing Sheets

OTHER PUBLICATIONS

Dor, Y. et al, Vascular endothelial growth factor and vascular adjustments to perturbations in oxygen homeostasis, AJP-Cell Physiology, 2001, pp. C1367-C1374, vol. 280(6).

Ikeda, E et al, Hypoxia-induced Transcriptional Activation and Increased mRNA Stability of Vascular Endothelial Growth Factor in C6 Glioma Cells, J. Biol. Chem., 1995, pp. 19761-19766, vol. 270(34).

Ferrara, N. et al, Pituitary follicular cells secrete a novel heparin-binding growth factor specific for vascular endothelial cells, BBRC, 1989. PP. 851-858, vol. 161(2).

Ferrara, N. et al, Molecular and biological properties of the vascular endothelial growth factor family of proteins, Endocr Rev, 1992, pp. 18-32, vol. 13(1).

Breier, G. et al, Expression of vascular endothelial growth factor during embryonic angiogenesis and endothelial cell differentiation, Development, 1992, pp. 521-532, vol. 114.

Keyt, B. et al. Identification of VEGF determinants for binding KDR and Flt-1 receptors. J Biol. Chem., 1996, pp. 5638-5646, vol. 271(10).

Ferrara, N. et al, Heterozygous embryonic lethality induced by targeted inactivation of the VEGF gene, Nature, 1996, pp. 439-442, vol. 380.

Carmeliet, P. et al, Abnormal blood vessel development and lethality in embryos lacking a single VEGF allele, Nature, 1996, pp. 435-439, vol. 380.

Barleon, B. et al, Migration of human monocytes in response to vascular endothelial growth factor (VEGF) is mediated via the VEGF receptor flt-1, Blood, 1996, pp. 3336-3343, vol. 87(8).

Neufeld, G. et al, Vascular endothelial growth factor (VEGF) and its receptors, FASEB. 1999, pp. 9-22, vol. 13.

Kim, K.J. et al, Inhibition of vascular endothelial growth factor-induced angiogenesis suppresses tumor growth in vivo, Nature, 1993, pp. 841-844, vol. 362.

Potgens, A. et al, Vascular permeability factor expression influences tumor angiogenesis in human melanoma lines xenografted to nude mice, Am. Jour. Pathol., 1995, pp. 197-209, vol. 146(1).

Claffrey, K.P. et al, Expression of vascular permeability factor/vascular endothelial growth factor by melanoma cells increases tumor growth, angiogenesis, and experimental metastasis, Cancer Res., 1996, pp. 172-181, vol. 56(1).

Shweiki, D. et al, Vascular endothelial growth factor induced by hypoxia may mediate hypoxia-initiated angiogenesis, Nature, 1992, pp. 843-845, vol. 359.

Dvorak, H.F. et al, Vascular permeability factor/vascular endothelial growth factor, microvascular hyperpermeability and angiogenesis, Am J Pathol, 1995, pp. 1029-1039, vol. 146(5).

Benjamin, L.E. et al, Conditional switching of vascular endothelial growth factor (VEGF) expression in tumors: Induction of endothelial cell shedding and regression of hemangioblastoma-like vessels by VEGF withdrawl, PNAS. 1997. pp. 8761-8766, vol. 94.

Jain R.K. et al, Endothelial cell death, angiogenesis, and microvascular function after castration in an androgen-dependent tumor: Role of vascular endothelial growth factor, PNAS, 1998, pp. 10820-10825, vol. 95(18).

Holash, S.J. et al, New model of tumor angiogenesis: dynamic balance between vessel regression and growth mediated by angiopoietins and VEGF, Oncogene, 1999, pp. 5356-5362, vol. 18.

Gilead, A. et al, Dynamic remodeling of the vascular bed precedes tumor growth: MLS ovarian carcinoma spheroids implanted in nude mice, Neoplasia, 1999, pp. 226-230, vol. 1(3).

Benjamin, L.E. et al, Selective ablation of immature blood vessels in established human tumors follows vascular endothelial growth factor withdrawal, J Clin Invest., 1999, pp. 159-165, vol. 103(2).

Benjamin, L.E. et al, A plasticity window for blood vessel remodeling is defined by pencyte coverage of the preformed endothelial network and is regulated by PDGF-B and VEGF, Development, 1998, pp. 1591-1598, vol. 125(9).

Grosskreutz, C.L. et al, Vascular Endothelial Growth Factor-Induced Migration of Vascular Smooth Muscle Cells in Vitro, Microvascular Research, 1999, pp. 128-136. vol. 58.

Lindahl, P. et al, Pericyte Loss and Microaneurysm Formation in PDGF-B-Deficient Mice, Science, 1997, pp. 242-245, vol. 277.

Hellstrom, M. et al, Role PDGF-B and PDGFR-b in recruitment of vascular smooth muscle cells and pericytes during embryonic blood vessel formation in the mouse Development, 1999, pp. 3047-3055, vol. 126.

Davis, S. et al, Isolation of Angiopoietin-1, a Ligand for the TIE2 Receptor, by Secretion-Trap Expression Cloning, Cell, 1996, pp. 1161-1169, vol. 87.

Suri, C. et al, Requisite Role of Angiopoietin-1, a Ligand for the TIE2 Receptor, during Embryonic Angiogenesis, Cell, 1996. pp. 1171-1180. vol. 87.

Maisonpierre, P.C. et al, Angiopoietin-2, a Natural Antagonist for Tie2 That Disrupts in vivo Angiogenesis, Science, 1997, pp. 55-60. vol. 277.

Folkman, J. et al, Blood Vessel Formation: What Is Its Molecular Basis?. Cell, 1996, pp. 1153-1155. vol. 87.

Eggert, A. et al, High-Level Expression of Angiogenic Factors Is Associated with Advanced Tumor Stage in Human Neuroblastomas. Clin. Can. Res., 2000, pp. 1900-1908. vol. 6.

Loughna, S. et al, Angiopoietin and Tie signaling pathways in vascular development, Matrix Biol., 2001, pp. 319-325, vol. 20.

Folkman, J. Tumor angiogenesis: therapeutic implications. N. Engl. J. Med., 1971, pp. 1182-1186, vol. 285(21).

O'Reilly, M.S. et al, Angiostatin: a novel angiogenesis inhibitor that mediates the suppression of metaslases by a Lewis lung carcinoma, Cell, 1994, pp. 315-328, vol. 79.

O'Reilly, M.S. et al, Endostatin: an endogenous inhibitor of angiogenesis and tumor growth, Cell, 1997, pp. 277-285, vol. 88.

Anderson, A.R. et al, Continuous and discrete mathematical models of tumor-induced angiogenesis, Bull Math Biol., 1998, pp. 857-899. vol. 60(5).

Hahnfeldt, P. et al, Tumor development under angiogenic signaling: a dynamic theory of tumor growth, treatment response, and postvascular dormancy, Cancer Res., 1999, pp. 4770-4775, vol. 59.

Rolland, Y. et al, Modeling of the parenchymous vascularization and perfusion, Invest. Radiology, 1999, pp. 171-175, vol. 34(3).

Hayes, A.J. et al, Expression and function of angiopoietin-1 in breast cancer, Br. J. Can., 2000, pp. 1154-1160, vol. 83(9).

Ahmad, S.A. et al, Differential expression of angiopoietin-1 and angiopoietin-2 in colon carcinoma, Cancer, 2001, pp. 1138-1143, vol. 92.

Koga, K. et al, Expression of angiopoietin-2 in human glioma cells and its role for angiogenesis, Cancer Res., 2001, pp. 6248-6254, vol. 61.

Oh, H. et al, Hypoxia and Vascular Endothelial Growth Factor selectively up-regulate angiopoietin-2 in bovine microvascular endothelial cells, J. Biol. Chem., 1999, pp. 15732-15739, vol. 274(22).

Holash, J. et al, Vessel cooption, regression, and growth in tumors mediated by angiopoietins and VEGF, Science, 1999, pp. 1994-1998, vol. 284.

Mandriota, S.J. et al, Hypoxia-inducible angiopoietin-2 expression is mimicked by Iodonium compounds and occurs in the rat brain and skin in response to systemic hypoxia and tissue ischemia, Am. J. Pathol., 2000, pp. 2077-2089, vol. 156(6).

Beck, H. Expression of angiopoietin-1, angiopoietin-2, and Tie receptors after middle cerebral artery occlusion in the rat, Am. J. Pathol., 2000, pp. 1473-1483, vol. 157(5).

Stratmann, A. et al, Cell type-specific expression of angiopoietin-1 and angiopoietin-2 suggests a role in glioblastoma angiogenesis, Am. J. Pathol., 1998, pp. 1459-1466, vol. 153(5).

Kocher, A.A. et al, Neovascularization of ischemic myocardium by human bone-marrow-derived angioblasts prevents cardiomyocyte apoptosis, reduces remodeling and improves cardiac function, Nat. Med., 2001, pp. 430-436, vol. 7(4).

Gavin, J.B. et al, Microvascular involvement in cardiac pathology. J Mol Cell Cardiol., 1998, pp. 2531-2540, vol. 30(12).

Jain, A. et al, Production of cytokines. vascular endothelial growth factor. matrix metalloproteinases, and tissue inhibitor of metalloproteinases 1 by tenosynovium demonstrates its potential for tendon destruction rheumatoid arthritis, Arthritis Rheum., 2001, pp. 1754-1760, vol. 44(8).

Miller, J.W., Vascular endothelial growth factor and ocular neovascularization, Am. J. Pathol., 1997, pp. 13-23, vol. 151(1).

O'Toole, G. et al, A review of therapeutic angiogenesis and consideration of its potential applications to plastic and reconstructive surgery, Br. J. Plast. Surg., 2001, pp. 1-7, vol. 54(1).

Ferrara, N., Vascular endothelial growth factor and the regulation of angiogenesis, Recent Prog. Horm. Res., 2000, pp. 15-36, vol. 55.

Tong, S. et al, Numerical simulations of angiogenesis in the cornea, Microvasc Res., 2001, pp. 14-27, vol. 61(1).

N. Bellomo and L. Presziosi, Modelling and Mathematical Problems Related to Tumor Evolution and its Interaction with the Immune System, Mathematical and Computer Modelling, Aug 2000, pp. 413-452, vol. 32.

Stelios Kakolyris et al., Assessment of Vascular Maturation in Non-Small Cell Lung Cancer Using a Novel Basement Membrane Component, LH39: Correlation with p53 and Angiogenic Factor Expression, Nov. 1999, pp. 5602-5607, vol. 59(21).

Philip Hahnfeldt, Tumor Development under Angiogenic Signaling: A Dynamical Theory of Tumor Growth, Treatment Response, and Postvascular Dormancy, Oct. 1999, pp. 4770-4775, vol. 59(19).

L. Arakelyan et al., A Computer Algorithm Describing the Process of Vessel Formation and Maturation, and its Use for Predicting the Effects of Anti-angiogenic and Anti-Maturation Therapy on Vascular Tumor Growth, Dec. 2002, pp. 203-214, vol. 5(3).

* cited by examiner

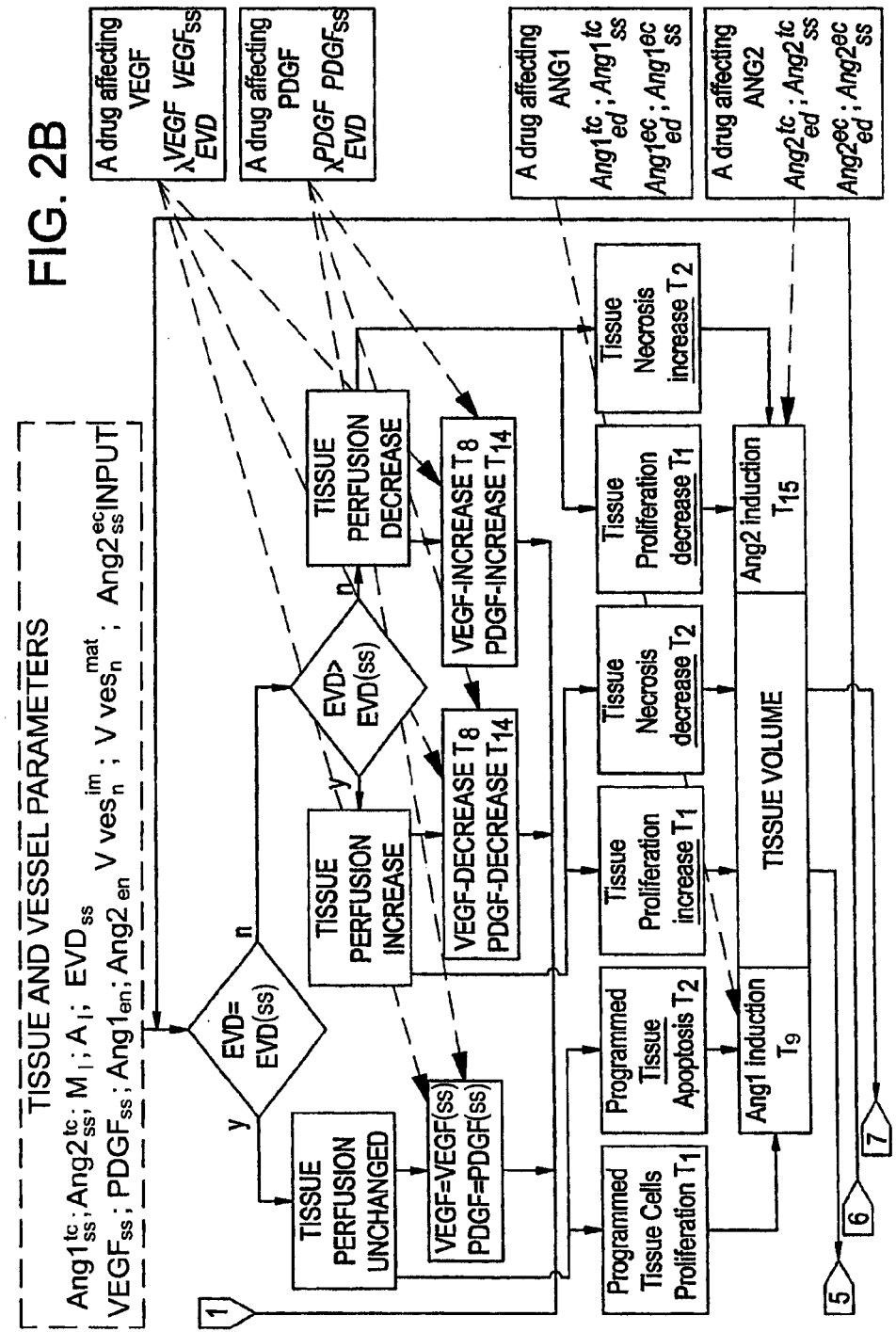

$D_d = 2.5$ $D_d = 4$ $D_d = 4.5$ $D_d = 5$

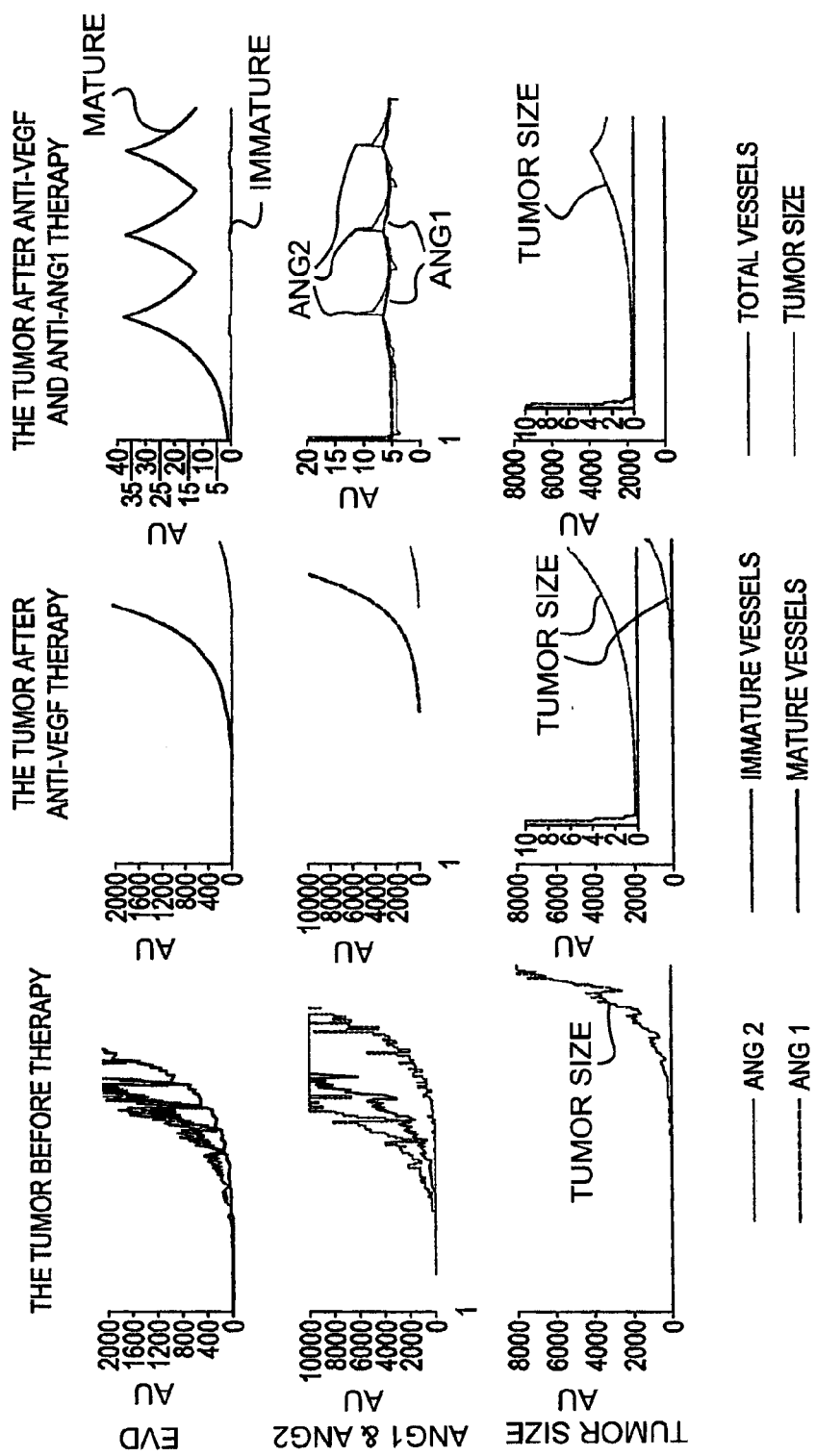

FIG. 5A

| Parameter/term | Definition |
|---|---|
| VEGF | Vascular Endothelial Growth Factor |
| EC | Endothelial Cell |
| PDGF | Platelet Derived Growth Factor |
| Ang1 | Angiopoietin 1 |
| Ang2 | Angiopoietin 2 |
| Tie 2 | Angiopoietin 1/2 receptor |
| A | VEGF concentration below which no endothelial cells proliferation takes place |
| B | Minimal number of receptors for VEGF above which endothelial cells proliferation takes place |
| C | The minimal number of free pericytes which stimulates the onset of maturation of immature vessels |
| K | Ang 1/Ang 2 ratio below which mature vessels are destabilized, and above which maturation of immature vessels is enabled |
| n | Moment of calculation of discrete parameters |
| $V_n^{tis}$ | Tissue volume |
| $Vves_n^{im}$ | Immature vessel volume |
| $Vves_n^{mat}$ | Mature vessel volume |
| EVD | Effective vessel density |
| $EVD_n$ | Effective vessel density in moment n |
| $EVD_{ss}$ | The EVD value for which the system is in steady state (ss) |
| $EVD_n^{im}$ | Density of immature vessels |
| $EVD_n^{mat}$ | Density of mature vessels |
| $d^{im}$ | Coefficient of efficiency of immature vessel |
| $d^{m}$ | Coefficient of efficiency of mature vessel |
| $A^{im \Rightarrow new}$ | Generation coefficient of immature vessels by immature vessels |
| $A^{mat \Rightarrow new}$ | Generation coefficient of immature vessels by mature vessels |
| $A^{mat \Rightarrow im}$ | The mature vessel destabilization coefficient |
| $A^{im \Rightarrow mat}$ | The immature vessel maturation coefficient |
| $A^{im \Rightarrow reg}$ | The immature vessel degeneration coefficient |
| $\lambda_{im}^{ec}$ | Coefficient of EC proliferation from one unit of immature vessels |
| $\lambda_{mat}^{ec}$ | Coefficient of EC proliferation from one unit of mature vessels |
| $\rho_{ec}^{im}$ | VEGF receptors density |
| $\rho_{ec}^{im}$ | VEGF receptors density |
| $\mu_{ec}$ | Coefficient of EC death |
| $\mu_{im}$ | Speed of immature vessel regression |
| $\mu_{mat}^{im}$ | Speed of mature vessel destabilization |

FIG. 5B

| Symbol | Description |
|---|---|
| $\lambda_{im}^{mat}$ | Speed of immature vessels maturation |
| $\rho_{mat}^{per}$ | The number of free pericytes necessary for the maturation of one unit volume of immature vessels |
| $N_{per}$ | Number of free pericytes |
| $VEGF_{tr}$ | VEGF concentration below which endothelial cells, both in the free state as well as in the bound state incorporated into immature blood vessels, are subject to apoptosis |
| $VEGF_{m}$ | Minimal secretion level of VEGF |
| $VEGF_{ss}$ | VEGF secretion level at the steady state of the system |
| $VEGF_{max}$ | Maximal secretion level of VEGF |
| $\lambda_{EVD}^{VEGF}$ | Factor describing a modifications in VEGF induction, when EVD is changed to 1 unit |
| $T_{n-1}^{VEGF}$ | VEGF half-life time |
| $PDGF_{m}$ | Minimal secretion level of PDGF |
| $PDGF_{ss}$ | PDGF secretion level at the steady state of the system |
| $PDGF_{max}$ | Maximal secretion level of PDGF |
| $\lambda_{EVD}^{PDGF}$ | Factor describing modification in PDGF induction, when EVD is changed to 1 unit |
| $T_{n-1}^{PDGF}$ | PDGF half-life time |
| $Ang2_{ss}$ | Ang2 secretion at the steady state of the system |
| $Ang2_{en}^{ec}$ | Minimal amount of Ang2 generated by 1 endothelial cell |
| $Ang2_{ss}^{ec}$ | Amount of Ang2 generated by 1 endothelial cell at ss |
| $Ang2_{ed}^{ec}$ | Factor describing modification in Ang2 induction by 1 endothelial cell, when EVD is changed to 1 unit |
| $Ang2_{en}^{tc}$ | Minimal amount of Ang2 generated by 1 tissue cell |
| $Ang2_{ss}^{tc}$ | Amount of Ang2 generated by 1 tissue cell at ss |
| $Ang2_{ed}^{tc}$ | Factor describing modification in Ang2 induction by 1 tissue cell, when EVD is changed to 1 unit |
| $T_{n-1}^{Ang2}$ | Ang2 half-life time |
| $\rho_{Vms,h}^{ec}$ | EC density in 1 volume unit of immature vessels |
| $Ang1_{ss}$ | Ang1 secretion at the steady state of the system |
| $Ang1_{en}^{ec}$ | Minimal amount of Ang1 generated by 1 endothelial cell |
| $Ang1_{ss}^{ec}$ | Amount of Ang1 generated by 1 endothelial cell at ss |
| $Ang1_{en}^{tc}$ | Minimal amount of Ang1 generated by 1 tissue cell |
| $Ang1_{ss}^{tc}$ | Amount of Ang1 generated by 1 tissue cell at ss |
| $Ang1_{ed}^{tc}$ | Factor describing modification in Ang1 induction by 1 tissue cell, when EVD is changed to 1 unit |
| $T_{n-1}^{Ang1}$ | Ang1 half-life time |

FIG. 5C

| | |
|---|---|
| $\lambda_{bou}^{per}$ | Coefficient of pericyte proliferation from one bound pericyte |
| $\lambda_{fr}^{per}$ | Coefficient of pericyte proliferation from one free pericyte |
| $\lambda$ | Tissue cell proliferation rate |
| $\mu$ | Tissue cell death rate |
| $\varphi$ | ln2 = 0.6931472, used as a factor of conformity |
| $\varepsilon_1 \varepsilon_2$ | Mathematical constants |
| $M_1$ | Mitotic index |
| $A_1$ | Apoptotic index |
| $r_{n-1}$ | Exponential cell growth rate |
| $T_0$ | Resolution time |
| $T_1$ | Mitotic time |
| $T_2$ | Apoptotic time |
| $T_3$ | Generation time of immature vessels by immature vessels |
| $T_4$ | Immature vessel degeneration time |
| $T_5$ | Generation time of immature vessels by mature vessels |
| $T_6$ | Immature vessel maturation time |
| $T_7$ | Mature vessel destabilization time |
| $T_8$ | VEGF generation time |
| $T_9$ | Ang1 generation time by tissue cell |
| $T_{10}$ | Ang2 generation time by EC |
| $T_{11}$ | Ang1 generation time by EC |
| $T_{12}$ | Pericyte proliferation time from one bound pericyte |
| $T_{13}$ | Pericyte proliferation time from one free pericyte |
| $T_{14}$ | PDGF generation time |
| $T_{15}$ | Ang2 generation time by tissue cell |
| $T_{16}$ | Endothelial cell death time |

TREATMENT PROTOCOL GENERATION FOR DISEASES RELATED TO ANGIOGENESIS

I.A. RELATED APPLICATIONS

This application claims priority from a U.S. Provisional Patent Application Ser. No. 60/330,592 filed Oct. 25, 2001, the contents of which are incorporated herein by reference.

I.B. FIELD

The present disclosure generally teaches techniques related to diseases and processes involving Angiogenesis. More particularly it teaches techniques for generating treatment protocols for diseases where angiogenesis is a factor. The techniques are also applicable to normal processes involving Angiogenesis even if no disease is present.

I.C. BACKGROUND

1. References

The following papers provide useful background information, for which they are incorporated herein by reference in their entirety, and are selectively referred to in the remainder of this disclosure by their accompanying reference numbers in brackets (i.e., <3> for the third numbered paper by Yangopoulos et al):

<1> Folkman J. (1995) Angiogenesis in cancer, vascular, rheumatoid and other disease. Nat. Med. 1(1):27-31.

<2> Carmeliet P., Jain R. K. (2000) Angiogenesis in cancer and other diseases. Nature. 407: 249-257. 14 Sep. 2000.

<3> Yangopoulos G D, Davis S., Gale N W., Rudge J S., Wiegand S J., Holash J. (2000) Vascular-specific growth factors and blood vessel formation. Nature. 407: 242-248. 14 Sep. 2000.

<4> Kerbel R. S, (2000) Tumor angiogenesis: past, present and the near future. Carcinogenesis. 21. 3: 505-515. March 2000.

<5> Danielsen T., Rofstad E K (2000). The constitutive level of vascular endothelial growth factor (VEGF) is more important than hypoxia-induced VEGF up-regulation in the angiogenesis of human melanoma xenografts. British Journal of Cancer. 82(9): 1528-1534.

<6> Dor Y., Porat R., Keshet E (2001) Vascular endothelial growth factor and vascular adjustments to perturbations in oxygen homeostasis. AJP-Cell Physiology. 280. 6: C1367-C1374. June 2001.

<7> Ikeda E., Achen M G., Breier G., Risau W. (1995). Hypoxia-induced Transcriptional Activation and Increased mRNA Stability of Vascular Endothelial Growth Factor in C6 Glioma Cells. J Biol. Chem. 270. 34: 19761-19766, Aug. 25, 1995.

<8> Ferrara N, Henzel W J (1989) Pituitary follicular cells secrete a novel heparin-binding growth factor specific for vascular endothelial cells. Biochem Biophys Res Commun. 161:851-858

<9> Ferrara N, Houck K, Jakeman L, Leung D W (1992) Molecular and biological properties of the vascular endothelial growth factor family of proteins. Endocr Rev 13:18-32

<10> Breier G, Albrecht U, Sterrer S, Risau W 1992 Expression of vascular endothelial growth factor during embryonic angiogenesis and endothelial cell differentiation. Development 114:521-532

<11> Keyt B, Nguyen H, Berleau L, Duarte C, Park J, Chen H, Ferrara N (1996) Identification of VEGF determinants for binding Flt-1 and KDR receptors. Generation of receptor-selective VEGF variants by site-directed mutagenesis. J Biol Chem 271:5638-5646

<12> Ferrara N, Carver-Moore K, Chen H, Dowd M, Lu L, O'Shea K S, Powell-Braxton L, Hillan K J, Moore M W (1996) Heterozygous embryonic lethality induced by targeted inactivation of the VEGF gene. Nature 380:439-442

<13> Carmeliet P, Ferreira V, Breier G, Pollefeyt S, Kieckens L, Gertsenstein M, Fahrig M, Vandenhoeck A, Harpal K, Eberhardt C, Declercq C, Pawling J, Moons L, Collen D, Risau W, Nagy A (1996) Abnormal blood vessel development and lethality in embryos lacking a single VEGF allele. Nature 380:435-439

<14> Barleon B, Sozzani S, Zhou D, Weich H, Mantovani A, MarméD (1996) Migration of human monocytes in response to vascular endothelial growth factor (VEGF) is mediated via the VEGF receptor flt-1. Blood 87:3336-3343

<15> Neufeld G, Cohen T, Gengrinovitch S, Poltorak Z (1999) Vascular endothelial growth factor (VEGF) and its receptors. FASEB 13:9-22

<16> Kim K J, Li B, Winer J, Armanini M, Gillett N, Phillips H S, Ferrara N (1993) Inhibition of vascular endothelial growth factor-induced angiogenesis suppresses tumour growth in vivo. Nature 362:841-844

<17> Potgens A J, Lubsen N H, van Altena M C, Schoenmakers J G, Ruiter D J, de Waal R M (1995) Vascular permeability factor expression influences tumor angiogenesis in human melanoma lines xenografted to nude mice. Am J Pathol. 146(1):197-209.

<18> Claffey K P, Brown L F, del Aguila L F, Tognazzi K, Yeo K T, Manseau E J, Dvorak H F. (1996) Expression of vascular permeability factor/vascular endothelial growth factor by melanoma cells increases tumor growth, angiogenesis, and experimental metastasis. Cancer Res. 56(1):172-81

<19> Shweiki D, Itin A, Soffer D, Keshet E (1992) Vascular endothelial growth factor induced by hypoxia may mediate hypoxia-initiated angiogenesis. Nature 359:843-845

<20> Dvorak H F, Brown L F, Detmar M, Dvorak A M (1995) Vascular permeability factor/vascular endothelial growth factor, microvascular permeability and angiogenesis. Am J Pathol 146:1029-1039

<21> Benjamin L E, Keshet E (1997) Conditional switching of vascular endothelial growth factor (VEGF) expression in tumors: Induction of endothelial cell shedding and regression of hemangioblastoma-like vessels by VEGF withdrawal. PNAS 94: 8761-8766. August 1997

<22> Jain R K, Safabakhsh N, Sckell A, Chen Y, Jiang P, Benjamin L E, Yuan F, Keshet E (1998) Endothelial cell death, angiogenesis, and microvascular function after castration in an androgen-dependent tumor: Role of vascular endothelial growth factor. PNAS 95. 18: 10820-10825. Sep. 1, 1998

<23> Holash, S J, Wiegandand G D, Yancopoulos G D, (1999) New model of tumor angiogenesis: dynamic balance between vessel regression and growth mediated by angiopoietins and VEGF. Oncogene 18: 5356-5362

<24> Gilead A., Neeman M (1999) Dynamic remodeling of the vascular bed precedes tumor growth: MLS ovarian carcinoma spheroids implanted in nude mice. Neoplasia 1:226-230.

<25> Benjamin L E et al. (1999) Selective ablation of immature blood vessels in established human tumors follows vascular endothelial growth factor withdrawal. J Clin Invest. 103(2):159-65.

<26> Benjamin L E et al. (1998) A plasticity window for blood vessel remodelling is defined by pericyte coverage of the preformed endothelial network and is regulated by PDGF-B and VEGF. Development 125(9):1591-8.

<27> Cynthia L. Grosskreutz, Anand-Apte B, Duplaa C, Quinn T P, Terman B I, Zetter B, D'Amore P A (1999) Vascular Endothelial Growth Factor-Induced Migration of Vascular Smooth Muscle Cells in Vitro. Microvascular Research 58:128-136

<28> Lindahl P, Johansson B R, Levéen P, Betsholtz C (1997) Pericyte Loss and Microaneurysm Formation in PDGF-B-Deficient Mice. Science 277: 242-245 11 Jul. 1997

<29> Hellstrom M, Kal'n M, Lindahl P, Abramsson A, Betsholtz C (1999) Role of PDGF-B and PDGFR-b in recruitment of vascular smooth muscle cells. Development 126: 3047-3055

<30> Davis S, Aldrich T H, Jones P F, Acheson A, Compton D L, Jain V, Ryan T E, Bruno J, Radziejewski C, Maisonpierre P C, Yancopoulos G D (1996) Isolation of Angiopoietin-1, a Ligand for the TIE2 Receptor, by Secretion-Trap Expression Cloning. Cell 87: 1161-1169. December 1996

<31> Suri C, Jones P E, Patan S, Bartunkova S, Maisonpierre P C, Davis S, Sato T S, Yancopoulos G D (1996) Requisite Role of Angiopoietin-1, a Ligand for the TIE2 Receptor, during Embryonic Angiogenesis. Cell 87: 1171-1180. December 1996

<32> Maisonpierre P C, Suri C, Jones P F, Bartunkova S, Wiegand S J, Radziejewski C, Compton D, McClain J, Aldrich T H, Papadopoulos N, Daly T J, Davis S, Sato T N, Yancopoulos G D (1997) Angiopoietin-2, a Natural Antagonist for Tie2 That Disrupts in vivo Angiogenesis. Science 277. 5322: 55-60. 4 Jul. 1997

<33> Folkman J, D'Amore P A (1996) Blood Vessel Formation: What Is Its Molecular Basis?. Cell 87: 1153-1155. December 1996

<34> Eggert A, Ikegaki N, Kwiatkowski J, Zhao H, Brodeur G M, Himelstein B P (2000) High-Level Expression of Angiogenic Factors Is Associated with Advanced Tumor Stage in Human Neuroblastomas. Clinical Cancer Research 6: 1900-1908

<35> Loughna S, and Sato T N. (2001) Angiopoietin and Tie signaling pathways in vascular development. Matrix Biol. 20:319-25.

<36> Folkman, J. (1971) Tumor angiogenesis: therapeutic implications. N. Engl. J. Med. 285:1182-1186.

<37> O'Reilly, M. S. et al. (1994) Angiostatin: a novel angiogenesis inhibitor that mediates the suppression of metastases by a Lewis lung carcinoma. Cell. 79:315-328.

<38> O'Reilly, M. S. et al. (1997) Endostatin: an endogenous inhibitor of angiogenesis and tumor growth. Cell. 88:277-285.

<39> Anderson A R and Chaplain M A (1998) Continuous and discrete mathematical models of tumor-induced angiogenesis. Bull Math Biol. 60(5):857-99.

<40> Hahnfeldt P. et al. (1999) Tumor development under angiogenic signaling: a dynamic theory of tumor growth, treatment response, and postvascular dormancy. Cancer Res. 59:4770-5.

<41> Rolland, Y. et al. (1998) Modeling of the parenchymous vascularization and perfusion. Invest. Radiology 34:171-5.

<42> Hayes, A J et al. (2000) Expression and function of angiopoietin-1 in breast cancer. Br. J. Cancer 83:1154-60.

<43> Ahmad, S A et al. (2001) Differential expression of angiopoietin-1 and angiopoietin-2 in colon carcinoma. Cancer 92:1138-43.

<44> Koga K. et al. (2001) Expression of angiopoietin-2 in human glioma cells and its role for angiogenesis. Cancer Res. 61:6248-54.

<45> Oh H. et al. (1999) Hypoxia and Vascular Endothelial Growth Factor selectively up-regulate angiopoietin-2 in bovine microvascular endothelial cells. J Biol Chem 274: 15732-9.

<46> Holash J. et al. (1999) Vessel cooption, regression, and growth in tumors mediated by angiopoietins and VEGF. Science 284:1994-8.

<47> Mandriota S J et al. (2000) Hypoxia-inducible angiopoietin-2 expression is mimicked by Iodonium compounds and occurs in the rat brain and skin in response to systemic hypoxia and tissue ischemia. Am J Pathol 156: 2077-89.

<48> Beck H. (2000) Expression of angiopoietin-1, angiopoietin-2, and Tie receptors after middle cerebral artery occlusion in rats. Am J Pathol 157:1473-83.

<49> Stratmann A. et al. (1998) Cell type-specific expression of angiopoietin-1 and angiopoietin-2 suggests a role in glioblastoma angiogenesis. Am J Pathol 153:1459-66.

<50> Stegmann T J et al. (2000) [Induction of myocardial neoangiogenesis by human growth factors. A new therapeutic approach in coronary heart disease] Herz.; 25(6): 589-99.

<51> Kocher A A et al. (2001) Neovascularization of ischemic myocardium by human bone-marrow-derived angioblasts prevents cardiomyocyte apoptosis, reduces remodeling and improves cardiac function Nat. Med.;7(4): 430-6.

<52> Ciulla T A et al. (2001) Presumed ocular histoplasmosis syndrome: update on epidemiology, pathogenesis, and photodynamic, antiangiogenic, and surgical therapies. Curr Opin Opthalmol.; 12(6):442-9.

<53> Weber A J, De Bandt M. (2000) Angiogenesis: general mechanisms and implications for rheumatoid arthritis. Joint Bone Spine.; 67(5):366-83.

<54> Fearon U, Veale D J. (2001) Pathogenesis of psoriatic arthritis. Clin Exp Dermatol.; 26(4): 333-7.

<55> Healy D L et al. (1998) Angiogenesis: a new theory for endometriosis. Hum Reprod Update; 4(5): 736-40.

<56> Gustafsson T., Kraus W E. (2001) Exercise-induced angiogenesis-related growth and transcription factors in skeletal muscle, and their modification in muscle pathology. Front Biosci; 6: D75-89.

<57> Brizzi M F et al. (2001) The molecular mechanisms of angiogenesis: a new approach to cardiovascular diseases. Ital Heart J.; 2(2):81-92.

<58> Gavin J B et al. (1998) Microvascular involvement in cardiac pathology. J Mol Cell Cardiol.; 30(12): 2531-40.

<59> Karasek M A. (1999) Progress in our understanding of the biology of psoriasis. Cutis.; 64(5): 319-22.

<60> Kurz H. (2000) Physiology of angiogenesis. J Neurooncol.; 50(1-2): 17-35.

<61> Aiello L P. (1997) Vascular endothelial growth factor and the eye: biochemical mechanisms of action and implications for novel therapies. Ophthalmic Res; 29(5): 354-62.

<62> Jain A et al. (2001) Production of cytokines, vascular endothelial growth factor, matrix metalloproteinases, and tissue inhibitor of metalloproteinases 1 by tenosynovium demonstrates its potential for tendon destruction in rheumatoid arthritis. Arthritis Rheum; 44(8): 1754-60.

<63> Carmeliet P. (1999) Basic Concepts of (Myocardial) Angiogenesis: Role of Vascular Endothelial Growth Factor and Angiopoietin. Curr Interv Cardiol Rep.; 1(4): 322-335.
<64> Miller J W. (1997) Vascular endothelial growth factor and ocular neovascularization. Am J Pathol.; 151(1): 13-23.
<65> O'Toole G. et al. (2001) A review of therapeutic angiogenesis and consideration of its potential applications to plastic and reconstructive surgery. Br J Plast Surg.; 54(1): 1-7.
<66> Halin C. et al. (2001) Antibody-based targeting of angiogenesis. News Physiol Sci.; 16: 191-4.
<67> Ferrara N. (2000) Vascular endothelial growth factor and the regulation of angiogenesis. Recent Prog Horm Res.; 55: 15-35
<68> Simons M. et al. (2000) Clinical trials in coronary angiogenesis: issues, problems, consensus: An expert panel summary. Circulation 12;102(11):E73-86.
<69> Tong S and Yuan F (2001) Numerical simulations of angiogenesis in the cornea. Microvasc Res; 61(1): 14-27.

2. Introduction

For a better understanding of this disclosure, all the terms and parameters used in this disclosure are listed in the Table shown in FIG. 5.

Angiogenesis, or neovascularization, is a process of new blood vessel formation by budding from the existing ones. Neovascularization provides tissue with vital nutrients and growth factors and enables clearance of toxic waste products of cellular metabolism. Angiogenesis has been conventionally recognized as a biological mechanism of dual clinical effect. On the one hand, it allows survival of normal tissues when they become ischemic. That is, it enables functional development of normal tissues, for example, wound healing and embryogenesis. On the other hand, angiogenesis enables tumor tissue to grow and eventually spread.

Intensive research of angiogenesis during the last 15 years has led to better understanding of this complex process <1-7, 57-60>. However, cause and effect relationships in the process of angiogenesis are yet to be clarified. Moreover, the massive research in the field of angiogenic therapy still suffers from the lack of tools for predicting the potential effects of PRO-and ANTI-angiogenic factors.

The two major determinants of new vasculature formation are thought to be the genetic features of the tissue and the availability of oxygen and nutrients <5,6>. The dependence of vessel formation on nutrients or oxygen deprivation was shown to be mediated by vascular endothelial growth factor (VEGF), which is a potent inducer of endothelial cell (EC) proliferation and migration <8-15>. VEGF is preferentially expressed by tissue cells in the nutrient-deprived areas <7, 16-20, 61-64>. In contrast, basic nutrient-independent VEGF production by the tissue is determined by genetic factors <20>. Consequently, VEGF-induced angiogenesis depends on both the aforementioned vasculature growth determinants, namely genetics and nutrient/oxygen availability. VEGF-induced angiogenesis leads to increase in nutrient supply to the tissue. Accordingly, nutrient- and oxygen-dependent VEGF expression is down-regulated. When VEGF level becomes low enough, the newly formed blood vessels regress <21-26>, consequently leading to nutrients and oxygen deprivation again. This negative feedback can produce successive cycles of growth and regression of blood vessels. This phenomenon was demonstrated in the mouse xenograft tumor model <12>.

Blood vessels can be rendered insensitive to fluctuations of VEGF concentration by the process of maturation (coverage of capillaries by periendothelial cells 25,26). This process involves pericytes (smooth muscle-like cells) which form an outside layer covering the endothelial cells of the newly formed vessel. The major pericyte-stimulating factor is a platelet-derived growth factor (PDGF)<27-29>. Interactions between endothelial cells and pericytes, which apparently lead to maturation, are governed by the Angiopoietin system. This system includes two soluble factors—Angiopoietins 1 and 2 (Ang1 and Ang2, respectively), and their receptor, Tie2, which is specifically expressed on endothelial cells <30-34>. Ang1 is Tie2 agonist that promotes maturation, while Ang2 is its natural antagonist <31,32>. Regulation of Ang1 and Ang2 expression is not completely understood. According to recent publications it can be influenced by tumor cell—as well as endothelial cell—specific factors <35,42-49>. These factors depend on the tissue and the host type <42-44>, and are, taken into account in the presented model. High Ang 1/Ang 2 ratio and pericytes' presence induce maturation of newly formed vessels. Alternatively, low Ang 1/Ang 2 ratio induces destabilization of mature blood vessels, while newly formed vessels remain immature and susceptible to VEGF fluctuations <25>.

Therefore, it would be advantageous to have techniques for generating and selecting treatment protocols for diseases where angiogenesis is a factor. Further, it is also advantageous to adapt the techniques to study the progression of processes involving angiogenesis.

3. Clinical Significance

The clinical significance of angiogenesis as an "ultimate" target for cancer therapy was first recognized in 1971 by J. Folkman <36>, and got wide acceptance in early nineties after the discovery of the first specific anti-angiogenic substances <37,38>. Apparent advantages of this approach include its universality for different solid tumors, lack of prominent side effects and lack of resistance development during repetitive treatment cycles.

Angiogenesis is implicated in the pathogenesis of a variety of disorders: proliferative retinopathies, age-related macular degeneration, tumors, rheumatoid arthritis, psoriasis <1;51-56, 66, 67> and coronary heart diseases <50>. The use of exogenous agents to selectively target neovasculature, or stimulate the growth of new blood vessels into ischemic tissue, is a potentially revolutionary therapy in a wide variety of clinical specialties, which opens new avenues for the diagnosis and therapy of diseases where angiogenesis is a factor; such as, cancer, blinding ocular disorders, rheumatoid arthritis and others.<65, 66>.

4. Problems in Practicing Anti/Pro-Angiogenic Therapy

In order to establish optimal pro-angiogenic or anti-angiogenic treatment protocols (either as a monotherapy or in combination with chemotherapy or radiotherapy) the dynamics of angiogenesis must be better understood. Recent studies <25,26> have shown that newly formed vasculature is very dynamic e.g. blood vessels undergo constant remodeling that involves maturation in response to local levels of angiogenic and maturation factors. Mature and immature vessels may differentially respond to certain PRO and ANTI-angiogenic drugs during tissue growth, myocardial ischemia, macular degeneration and other diseases, leading to success or failure of the treatment <25>.

Mathematical models and computer simulation of angiogenesis and PRO- and ANTI-angiogenic therapy can be constructed, in order to predict the most promising treatment protocols thus eliminating the need for lengthy and expensive clinical trials.

5. Previous Mathematical Models

The construction of a mathematical model for angiogenesis includes I) in-depth understanding of the biology of angiogenesis, II) the selection of appropriate patient populations for clinical trials, choice of therapeutic end points and means of their assessment, choice of therapeutic strategy (gene versus protein delivery), route of administration, and the side effect profile.<68>

Several mathematical dynamic models have been proposed, each one of them constructed to illuminate specific aspects of angiogenesis <39-41>. Some of these models examine vascular tree formation in vitro, irrespectively of tumor dynamics, and consequently are not suitable for tumor growth modeling <39>. Others assume that the growing vascular tree is a subject to some optimization with regard to the target tissue perfusion <41>. This optimization, while possibly holding true for normal tissue development, can hardly account for tumor growth, since it is known that tumor vasculature is highly disorganized.

Logistic-type model, proposes by Hahnfeldt et al. <40>, analyzes the general vascular dynamics ("carrying capacity of current vascular tree") with regard to production of pro- and anti-angiogenic factors by the tumor. Analysis of experimental data of Lewis lung carcinoma growth in mice allowed the authors to estimate the model parameters and to examine the effects of anti-angiogenic factors angiostatin and endostatin. The main problematic assumption of this model is the constant production rates of these factors, as we know that VEGF, for example, production is tightly regulated by tissue hypoxia.

Model by Tong S and Yuan F<69> focused on two-dimensional angiogenesis in the cornea. The model considered diffusion of angiogenic factors, uptake of these factors by endothelial cells, and randomness in the rate of sprout formation and the direction of sprout growth.

None of the aforementioned models takes into account vasculature maturation and mature vessel destabilization, which are very fundamental constituents of angiogenesis dynamics. Moreover, these models, due to their relative abstraction, cannot account for drug-induced, or other molecular changes in angiogenic dynamics. Note that since PRO and ANTI-angiogenic drugs interfere with the dynamics described above at the molecular level, the model which can serve as a tool for predicting drug effect on this process must take into account all the molecular complexity of angiogenesis, including the dynamics of neovasculature maturation and mature vessel destabilization.

Therefore, it is desirable to provide techniques, including computer systems, that overcomes some of the disadvantages noted above.

SUMMARY

To realize the advantages discussed above, the disclosed teachings provide a computer-implemented method for determining an optimal treatment protocol for a disease related to angiogenesis, comprising creating an angiogenesis model including pro-angiogenesis and anti-angiogenesis factors. Effective vessel density (EVD) is incorporated as a factor regulating switching on and switching off of at least one component in the angiogenesis model. Effects of vasculature maturation and mature vessel destabilization are incorporated. Pro-angiogenesis and anti-angiogenesis factors, which can influence changes in state of a tissue, are selected. Effects of drugs in the pro-angiogenesis and anti-angiogenesis factors are incorporated. A plurality of treatment protocols in a protocol space is generated. A best treatment protocol based on pre-determined criteria is selected.

In another specific enhancement, the model comprises a tissue volume model, an immature vessel model and a mature vessel model.

In another specific enhancement, steps to regulate dynamics which influences EVD are incorporated.

In another specific enhancement, the model simultaneously accounts for tissue cell proliferation, tissue cell death, endothelial cell proliferation, endothelial cell death, immature vessel formation and immature vessel regression, immature vessel maturation and mature vessel destabilization.

In another specific enhancement, the model incorporates temporal parameters that characterize response rate of at least one element associated with angiogenesis.

More specifically, EVD is calculated by combining immature vessel density and mature vessel density.

In another specific enhancement, parameters incorporated into the model comprises tissue volume, number of free endothelial cells, number of free pericytes, volume of mature vessels, volume of immature vessels and concentration of regulator factors.

More specifically, the regulatory factors comprise vascular endothelial growth factor (VEGF), platelet derived growth factor (PDGF), angiopoietin 1 (Ang1) and angiopoietin 2 (Ang2).

More specifically, EVD is a function of a duration of insufficient perfusion and vice versa.

More specifically, the model incorporates threshold levels of regulatory factors and parameter ratios.

Even more specifically, the threshold level (thr) is at least one of: a) VEGF concentration below which no endothelial cells proliferation takes place (A); b) minimal number of receptors for VEGF above which endothelial cells proliferation takes place (B); c) VEGF concentration below which endothelial cells, both in the free state as well as when incorporated into immature blood vessels, are subject to apoptosis $VEGF_{thr}$; d) the minimal number of free pericytes which stimulates the onset of maturation of immature vessels (C); e) Ang 1/Ang 2 ratio below which mature vessels are destabilized, and above which maturation of immature vessels is enabled (K); f) EVD value that influences the rate of cell proliferation and death ($EVD_n$) and g) $EVD_{ss}$ value for which the system is in steady state (ss).

Even more specifically, the tissue volume model calculates the tissue volume by a process comprising: comparing EVD against $EVDS_{ss}$. If EVD is equal to $EVD_{ss}$ then use a programmed tissue cell proliferation and a programmed tissue cell death (apoptosis) to compute tissue volume. If $EVD>EVD_{ss}$ then use increased tissue proliferation and decreased tissue cell death to compute tissue volume. If $EVD<EVD_{ss}$ then use decreased tissue proliferation and increased tissue cell death to compute tissue volume.

Even more specifically, Ang1 and Ang2 induction are incorporated into appropriate steps above following the computation of tissue volume.

More specifically, the immature vessel model calculates the immature vessel volume by a process comprising comparing EVD against an $EVD_{ss}$. If EVD is equal to $EVD_{ss}$ then set VEGF to a $VEGF_{ss}$ and PDGF to a $PDGF_{ss}$. If $EVD>EVD_{ss}$ then use decreased VEGF and decreased PDGF. If $EVD<EVD_{ss}$ then use increased VEGF and increased PDGF. Compare VEGF against A. Factor endothelial cell proliferation if VEGF>A. Compare VEGF against a VEGF threshold. Factor free endothelial cell deaths if VEGF<VEGF threshold. Compare VEGF receptor number against B. If VEGF receptor number is less than B then consider no angiogenesis prior to computing immature vessel regression. If VEGF receptor number is not less than B then compute growth of immature vessels. If VEGF<A then consider no angiogenesis and compute immature vessel regression. Compute mature vessel volume based on growth immature vessels, immature vessel regression and mature vessel destabilization.

Even more specifically, immature vessel computation considers no maturation if Ang2/Ang1>K or if number of free pericytes<C.

Even more specifically, mature vessel destabilization considers ang1/Tie2 interaction blocking.

Even more specifically, no destabilization occurs if Ang2/Ang1 is not greater than K.

More specifically, the mature vessel model is computed using a procedure comprising computing immature vessels. Determine if Ang1/Ang2<K. Determine if number of free pericytes<C. Consider immature vessel maturation if both the above steps are false. Do not factor destabilization if number of free pericytes is not less than C.

More specifically, effects of a drug affecting EC proliferation are factored in computing immature vessels.

More specifically, effects of a drug affecting VEGF receptors are factored in computing immature vessels.

More specifically, effects of a drug affecting pericyte proliferation are factored in computing immature vessel computation.

More specifically, effects of a drug affecting VEGF are factored in computing immature vessels.

More specifically, effects of a drug affecting PEGF are factored in computing immature vessel computation.

More specifically, effects of a drug affecting Ang1 are factored in computing immature vessels.

More specifically, effects of a drug affecting Ang2 are factored in computing immature vessel computation.

In another specific enhancement, the model takes into account the duration of tissue cell proliferation, tissue cell death, endothelial cell proliferation, endothelial cell death, pericyte proliferation, immature vessel regression, immature vessel maturation and mature vessel destabilization.

In another specific enhancement, the model takes into account the duration of VEGF induction, PDGF induction, Ang1 and Ang2 induction by tissue cells and Ang1 and Ang2 induction by endothelial cells.

Another aspect of the disclosed teachings is an optimal treatment protocol for a disease related to angiogenesis, comprising an angiogenesis model including pro-angiogenesis and anti-angiogenesis factors; a treatment protocol space generator that generates a protocol space of possible treatments for the disease; a treatment selector that selects an optimal protocol, wherein effective vessel density (EVD) is a factor regulating switching on and switching off of at least one component in the angiogenesis model; wherein the model incorporates effects of vasculature maturation and mature vessel destabilization; and wherein the system is adapted to affect selection of pro-angiogenesis and anti-angiogenesis factors which can influence changes in state of a tissue and incorporating effects of drugs in the pro-angiogenesis and anti-angiogenesis factors.

A computer program product including computer readable media that comprises instructions to implement the above techniques on a computer are also part of the disclosed teachings.

BRIEF DESCRIPTION OF THE DRAWINGS

The above objectives and advantages of the disclosed teachings will become more apparent by describing in detail preferred embodiment thereof with reference to the attached drawings in which:

FIG. 4 shows graphs that illustrate the simulated effects of a combination of Anti-VEGF and Anti-Ang1 Drugs.

FIG. 5 (a)-(c) shows a table with description of parameters and terms used in the Equations included in the specification.

DETAILED DESCRIPTION

IV.A. Overview of Exemplary Implementations

The disclosed techniques are embodied in exemplary computer systems and exemplary flowcharts that describe algorithms which are implemented by computers. The implementations discussed herein are merely illustrative in nature and are by no means intended to be limiting. Also it should be understood that any type of computer can be used to implement the systems and techniques. An aspect of the disclosed teachings is a computer program product including computer-readable media comprising instructions. The instructions are capable of enabling a computer to implement the systems and techniques described herein. It should be noted that the computer-readable media could be any media from which a computer can receive instructions, including but not limited to hard disks, RAMs, ROMs, CDs, magnetic tape, internet downloads, carrier wave with signals, etc. Also instructions can be in any form including source code, object code, executable code, and in any language including higher level, assembly and machine languages. The computer system is not limited to any type of computer. It could be implemented in a stand-alone machine or implemented in a distributed fashion, including over the internet.

The technique shown in the flowchart take into account the dynamic interactions between tissue volume, angiogenesis (growth and regression of immature blood vessels), and vascular maturation and destabilization. The technique shown in the flowchart is combined with a quantitative mathematical model that is described in detail herein. A combination of the technique shown in the flowchart and the mathematical computations described would allow a skilled artisan to practice the disclosed technique; including for example, to quantify the dynamics of tissue vascularization and the effect of drug on this process at any given moment.

The technique describes the interactions between molecular regulatory factors, cell types and multi-cellular structures (such as vessels) which together influence the tissue dynamics. The technique takes into account the temporal parameters which characterize the response rates of each one of the elements included in the angiogenesis process.

The technique includes a series of simulation steps. The parameter values that are outputted from each simulation step are taken as initial conditions for the next simulation step.

These parameter values are compared with the threshold levels. Their current values are calculated according to the arrows shown in the flowchart of FIG. 1. At least six major processes are taken into account simultaneously, namely tissue cell proliferation and death, endothelial cell proliferation and death, immature vessel formation and regression, immature vessel maturation and mature vessel destabilization, and possibly others.

Figure 1A:
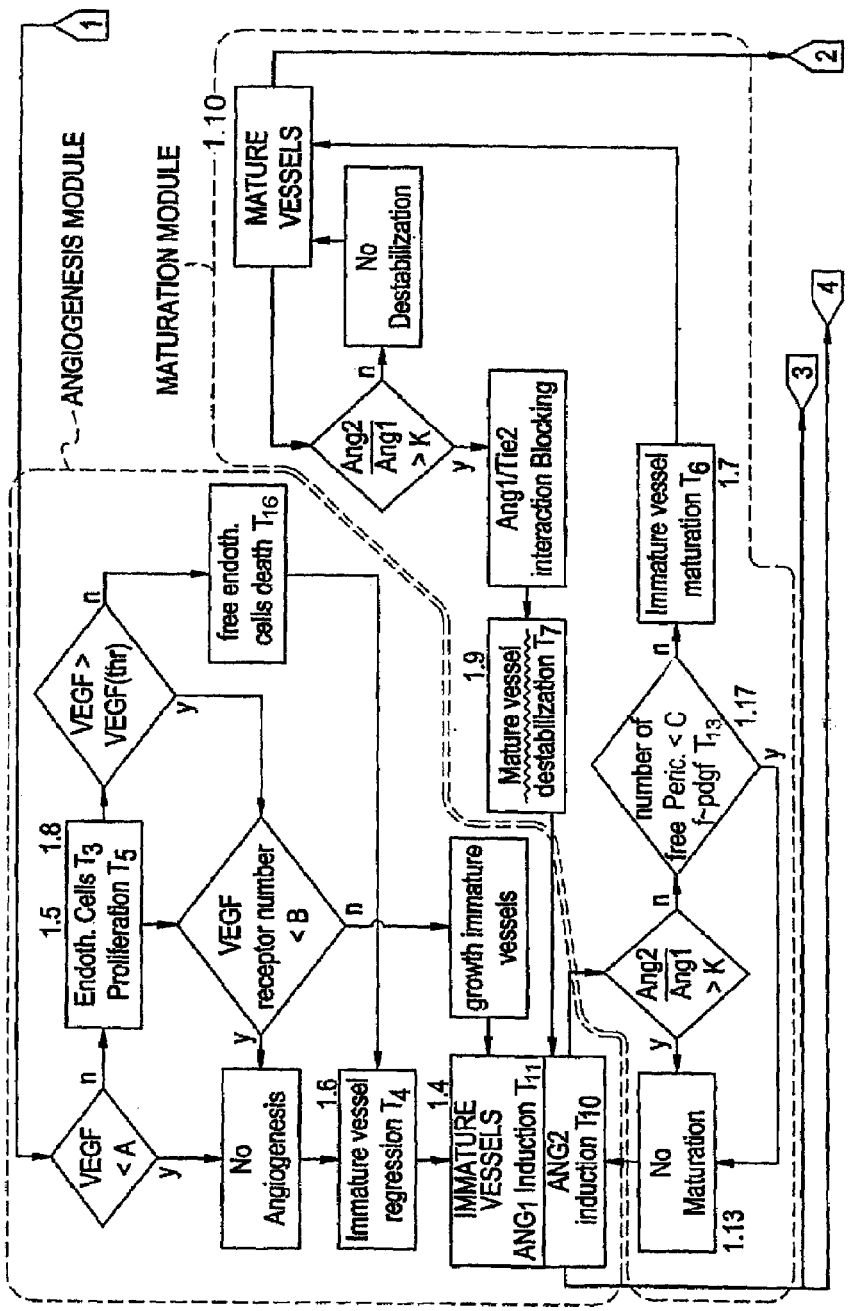
FIG. 1 depicts a flowchart that shows an implementation of the overall techniques.
Figure 1B:
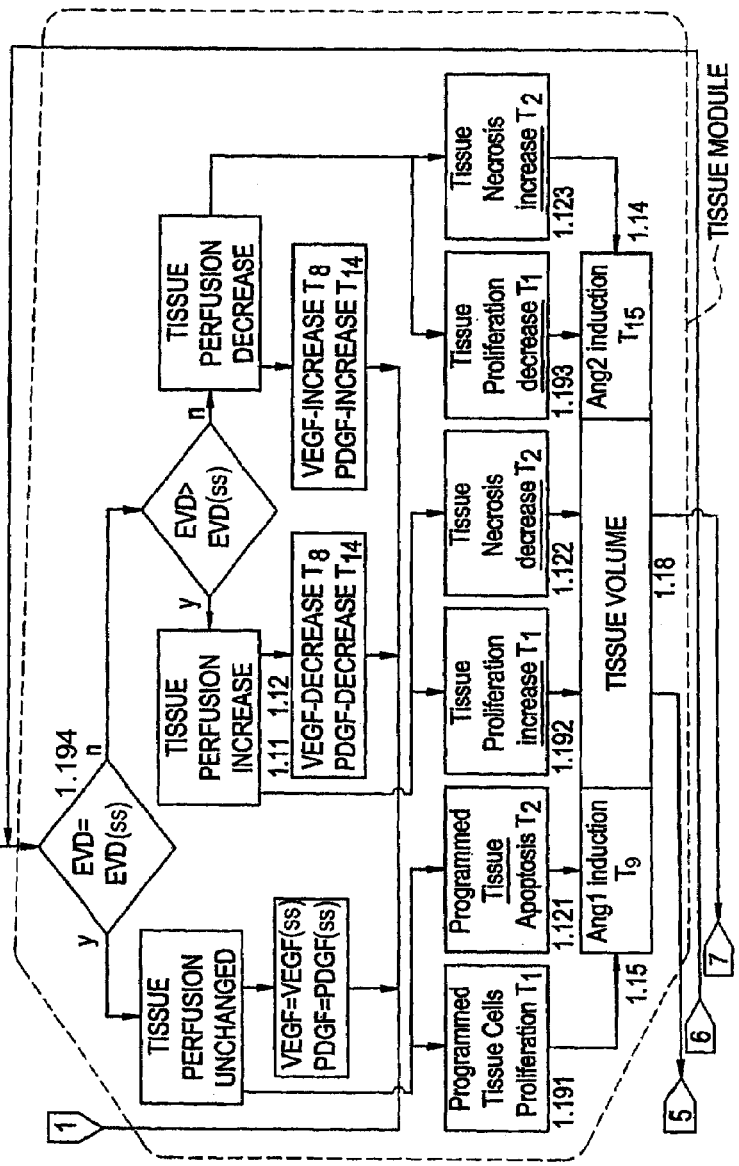
Figure 1C:
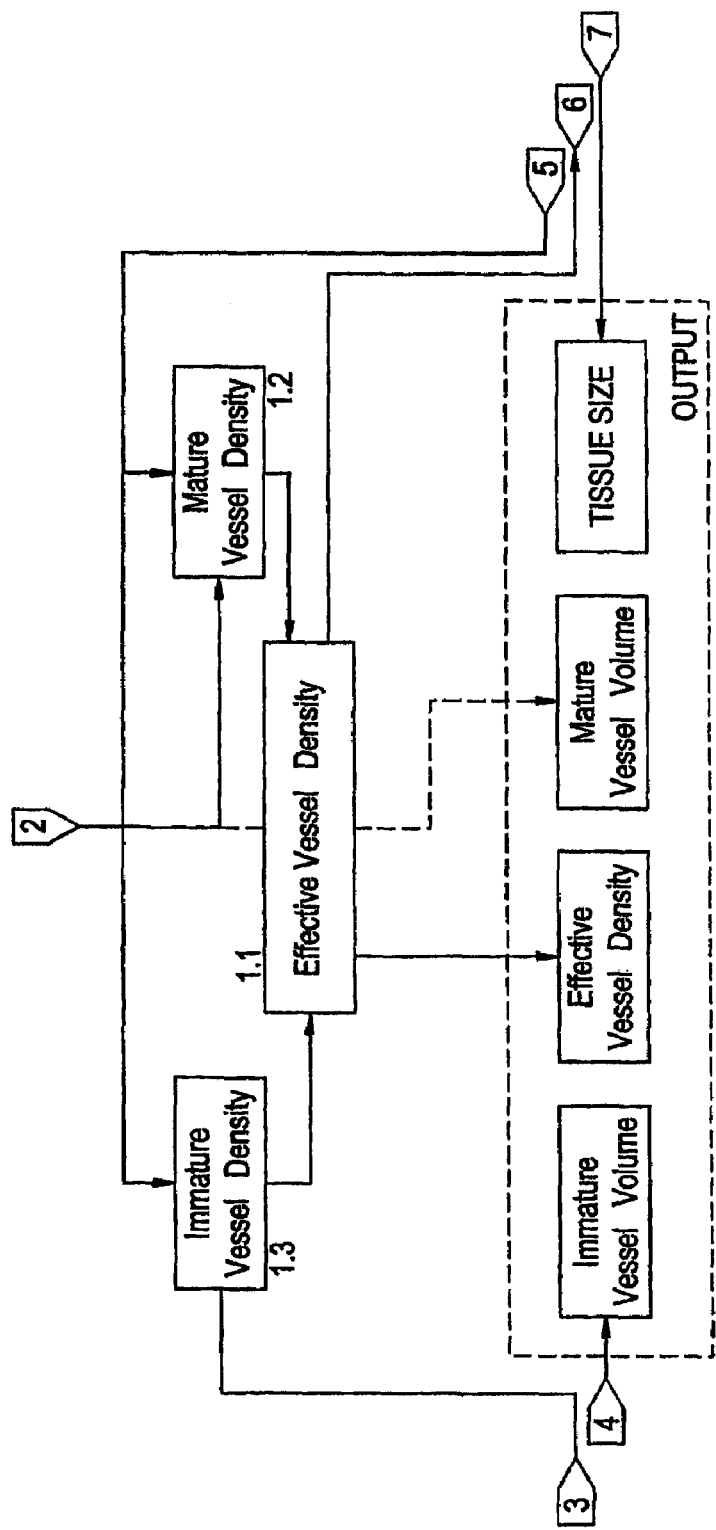

The techniques depicted in FIG. 1 include three interconnected modules: tissue cell proliferation, angiogenesis (immature vessels growth) and maturation (formation and destabilization of mature vessels). Further, each module operates on three scales: molecular, cellular and macroscopic (namely, vessel densities and tissue volume).

The tissue module includes tissue cell proliferation sub-module and cell death sub-module. Further, each sub-module is subdivided into i) time-invariant, cell type-specific, genetically determined sub-block, and ii) time-variant, nutrient-dependent sub-block. Nutrient-dependent cell proliferation and nutrient-dependent cell death rates are directly or inversely proportional, respectively, to the effective vascular density (EVD), which is the perfused part of vascular tree <40>.

Two additional quantities are calculated in the tissue module, namely VEGF and PDGF production. They are inversely related to EVD so that increasing nutrient depletion results in increasing secretion of these pro-angiogenic factors <7-9>. The tissue growth module interacts with the angiogenesis and the maturation modules via the relevant regulatory proteins.

In the angiogenesis module, volume of immature vessels is calculated. Immature vessel volume increases proportionally to VEGF concentration, if VEGF is above a given threshold level. The volume regresses if VEGF is below a given, possibly different, threshold level. The latter threshold is generally referred to as "survival level"<21-24>.

In the maturation module, volume of mature vessels is calculated according to pericyte concentration <41-43> and according to the Ang1/Ang2 ratio <44>. Pericytes proliferate proportionally to PDGF concentration <25-26>. Ang1 and Ang2 are continuously secreted by tissue cells and immature vessels, respectively <27, 28, 32-34, 41-43, 45>. Additionally, Ang1 and Ang2 can be secreted by tissue cells, if the latter are nutrient-depleted <45>. It is assumed that maturation of immature vessels occurs if pericytes concentration and Ang1/Ang2 ratio are above their respective threshold levels, while under these thresholds immature vessels do not undergo maturation, while mature vessels undergo destabilization and become immature <29-33>.

It is clear that the parameters used in the technique can include tissue volume (determined as a function of tissue cell number); number of free endothelial cells and pericytes; volume of immature and mature vessels; and concentrations of the regulatory factors such as VEGF, PDGF, Ang1 and Ang2.

Moreover, several relative parameters (ratios) are calculated, such as Ang2/Ang1, immature vessel density and mature vessel density (denoting vessels volume divided by tissue volume). The latter two densities are combined into effective vessel density, EVD. EVD is a critical model variable, which at any moment determines tissue cell proliferation and death, as well as the production of factors, such as VEGF and PDGF. Resistance of tissue cells to anti-angiogenic drugs may emerge from tissue adaptation to hypoxia.

In order to account for the possible adaptation of tissue cells to insufficient nutrition and to hypoxia it is assumed that EVD is a function of the duration of insufficient perfusion, (denoted below by EVDn).

The technique takes into account the threshold levels of regulatory factors and parameter ratios, such as:

VEGF concentration below which no endothelial cells proliferation takes place (denoted below by A);

The minimum number of receptors for VEGF above which endothelial cells proliferation takes place (denoted below by B);

VEGF concentration below which endothelial cells (both in the free state as well as when incorporated into immature blood vessels) are subject to apoptosis (this is denoted below by $VEGF_{thr}$);

The minimal number of free pericytes which stimulates the onset of maturation of immature vessels (denoted below by C);

The Ang 1/Ang 2 ratio below which mature vessels are destabilized, and above which maturation of immature vessels is enabled (denoted below by K).

The EVD value influences the rate of cell proliferation. The EVD value for which the system is in steady state (tissue cell proliferation rate being equal to tissue cell death rate) is denoted below by $EVDS_{ss}$. At $EVD>EVD_{ss}$ tissue cell proliferation prevails, so that tissue volume increases. At $EVD<EVD_{ss}$ tissue cell death prevails, and the tissue shrinks. The $EVD_{ss}$ is determined by genetic properties of a given tissue and a given host. VEGF, PDGF, Ang1 and Ang2 secretion level at the steady state of the system will be denoted by $VEGF_{ss}$, $PDGF_{ss}$, $Ang1_{ss}$, and $Ang2_{ss}$.

The inputs to the represented system include the tissue volume, blood vessel density, and the inherent parameters characterizing this tissue type at initiation of the process. The outputs at any given moment are parameters like tissue volume, mature and immature vessels sizes, and EVD.

IV.B. Detailed Description of the Exemplary Implementation

The flowchart shown in FIG. 1 is discussed in detail herein with reference to specific mathematical equations describing the principal interactions affecting vascular tissue growth. The technique describes the interrelationships between tissue growth, the formation of new vessels (angiogenesis) and the maturation of the newly formed vessels. The interactions occur across three organization levels: molecular, cellular, and physiological levels. The arrows in the flowchart indicate the specific module interactions. The rectangular boxes indicate the point at which a specific sub-process calculation occurs. The parameter $T_x$ in a box denotes the characteristic reaction time of the action calculated in the box. The diamonds indicate the conditions, which determine the direction of processes.

$EVD_{ss}$ is the value for which the system is in steady state. $VEGF_{ss}$ is the VEGF secretion level at the steady state of the system. $VEGF_{thr}$ is the VEGF concentration below which endothelial cells, both in the free state as well as when incorporated into immature blood vessels, are subject to apoptosis. $PDGF_{ss}$ is the PDGF secretion level at the steady state of the system.

In this mathematical model $EVD_n$ in a certain moment n is represented as the sum of a density of immature ($EVD_n^{im}$) and density of mature vessels ($EVD_n^{mat}$) at the moment "n".

$$EVD_n = EVD_n^{im} + EVD_n^{mat}; \qquad (1)$$

Figure 2A:
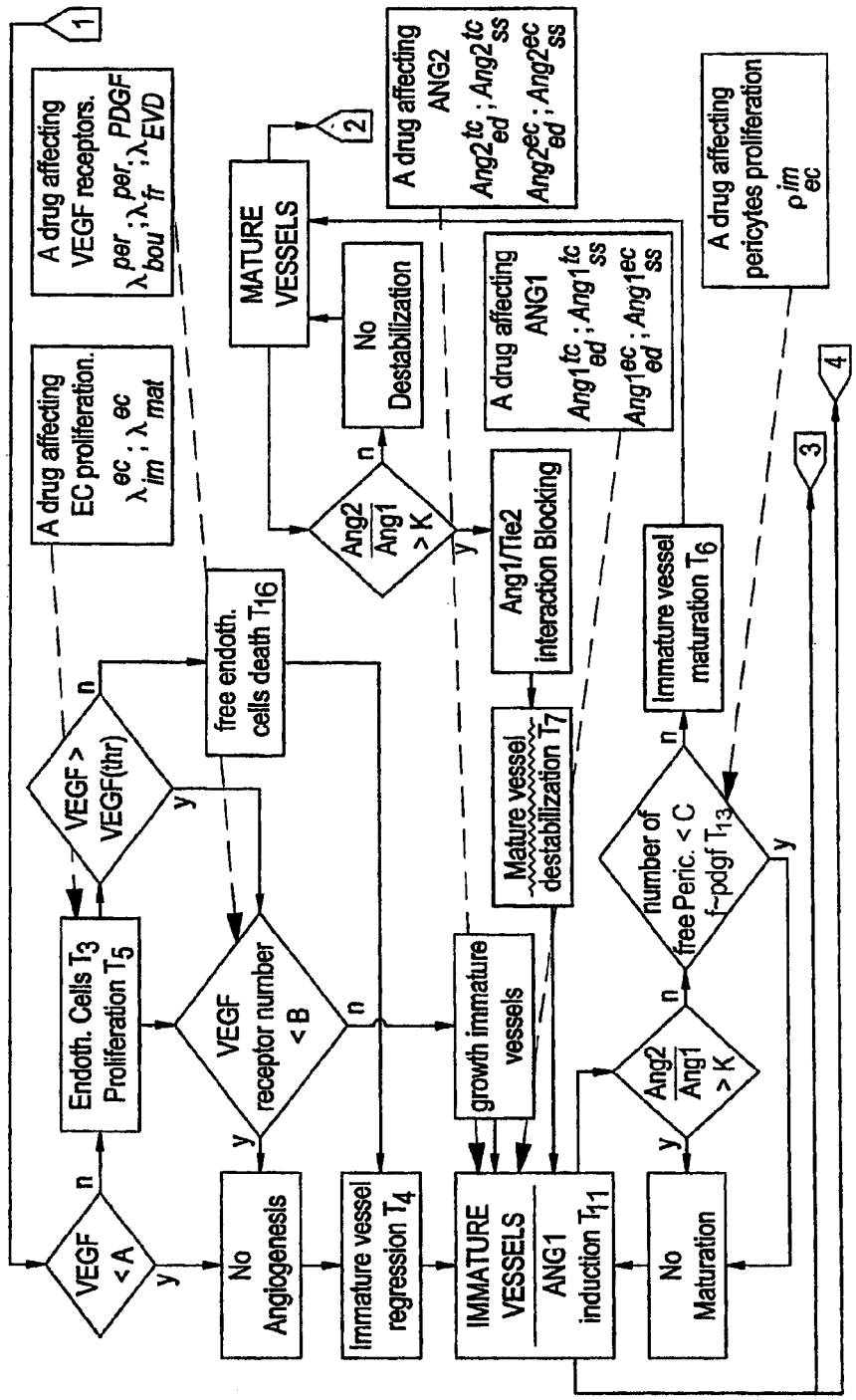
FIG. 2 depicts the flowchart of FIG. 1 with possible effects due to Pro-Angiogeneses and Anti-Angiogeneses drugs.
Figure 2C:
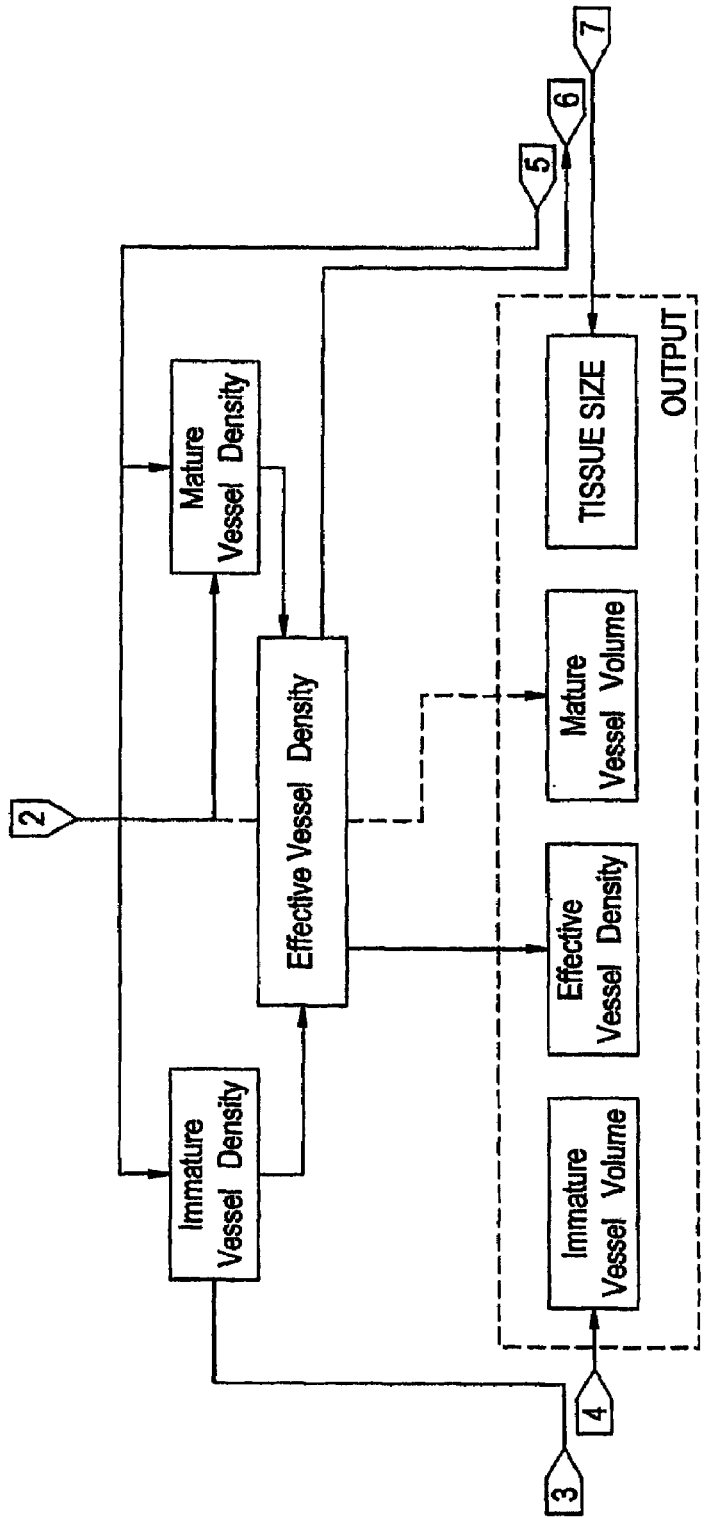
Figure 3A:
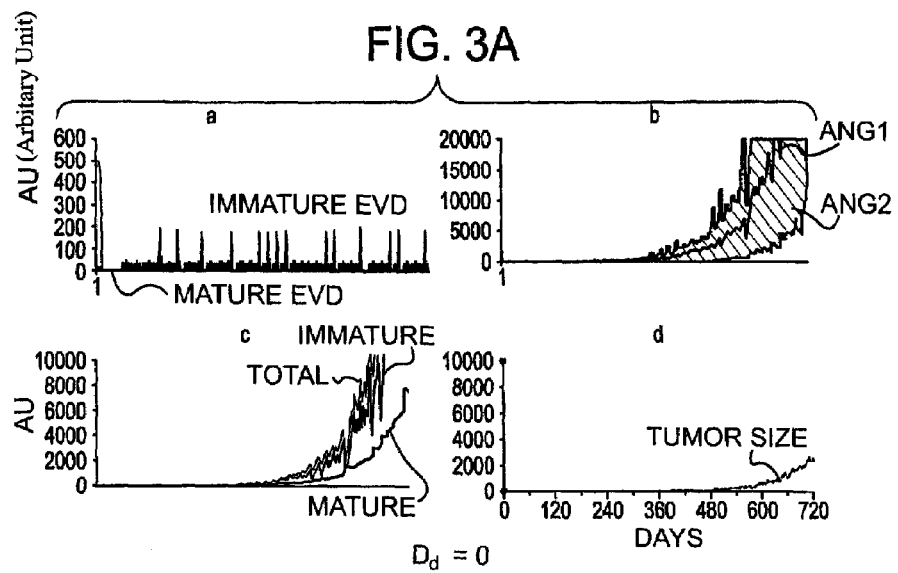
FIG. 3 shows graphs that illustrate the simulated effects of Anti-VEGF Drugs.
Figure 3B:
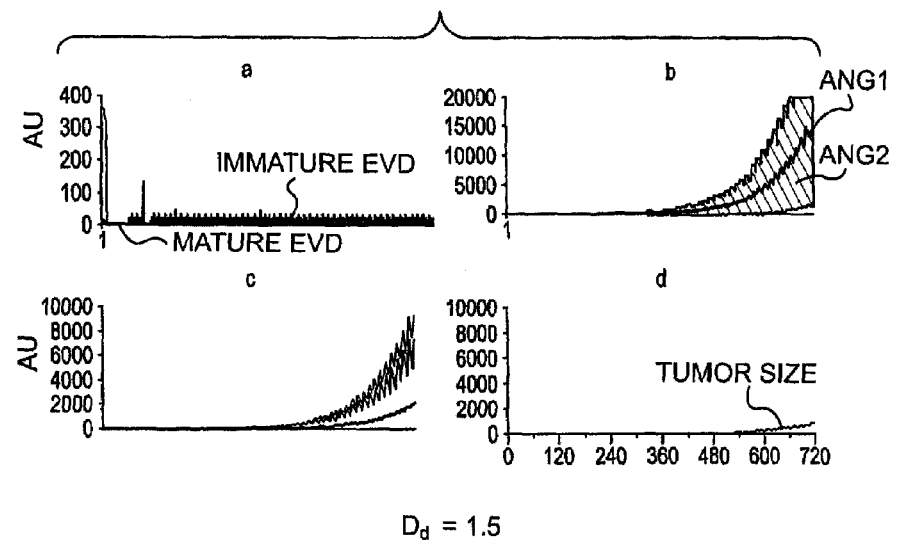
Figure 3C:
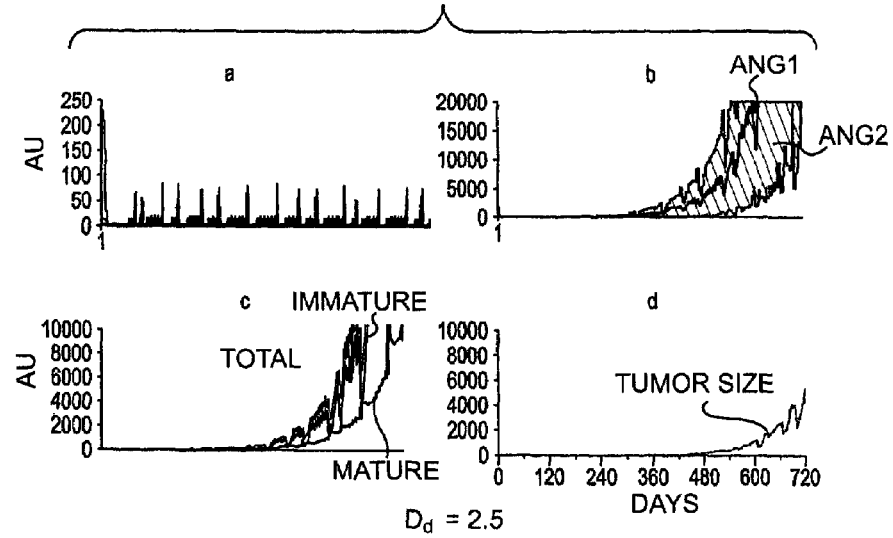
Figure 3D:
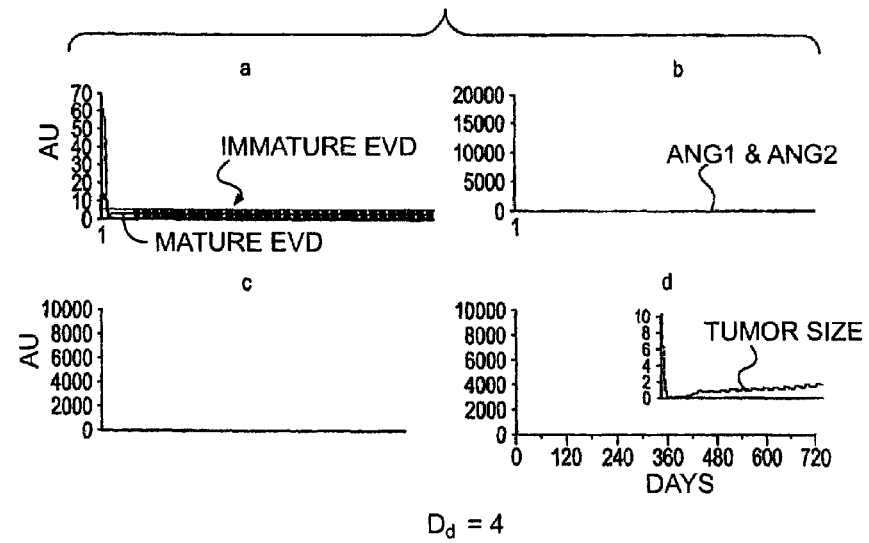
Figure 3E:
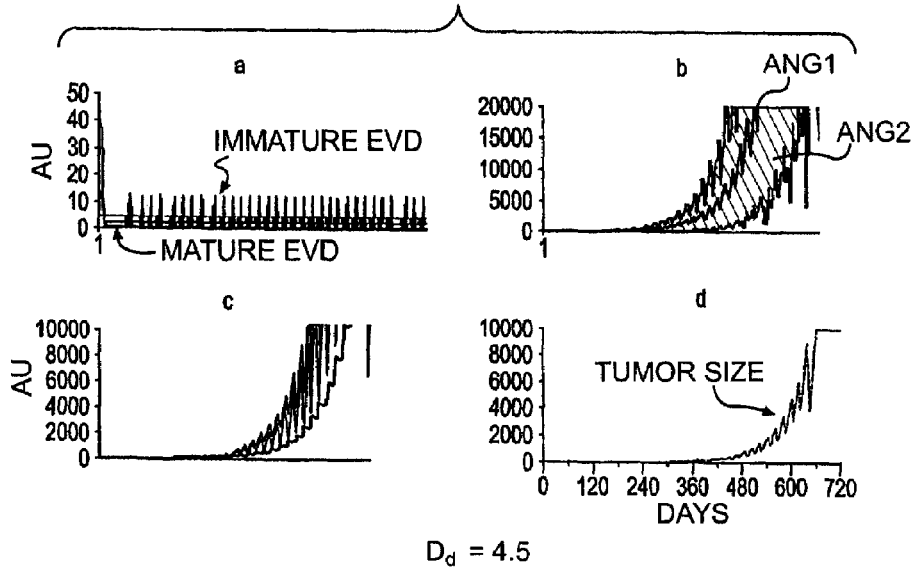
Figure 3F:
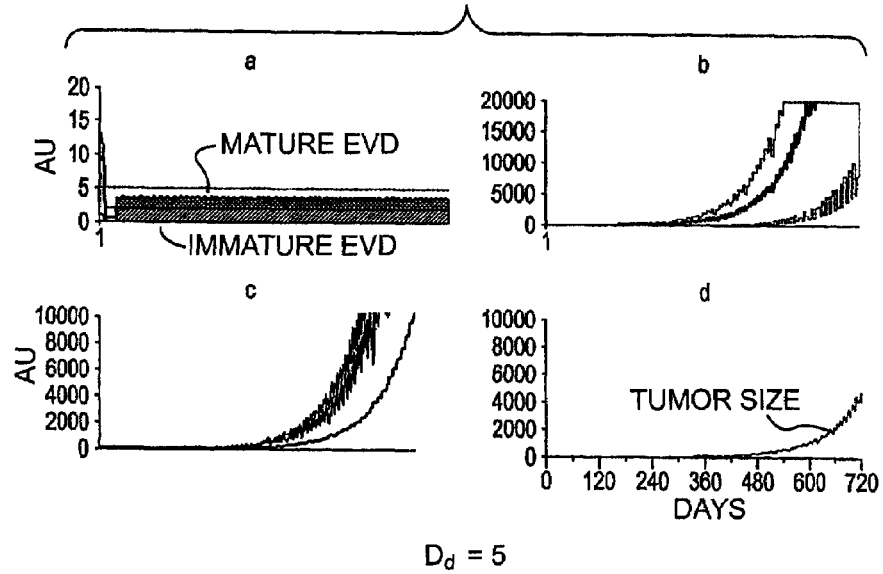

In FIGS. 1 and 2 the effective vessel density as discussed above is calculated in block 1.1. The mature and immature vessel densities, in turn, are calculated in blocks 1.2 and 1.3 using the following equations:

$$EVD_n^{mat} = \frac{\alpha^{mat} * Vves_n^{mat}}{V_n^{tis}}; \quad (2)$$

$$EVD_n^{im} = \frac{\alpha^{im} * Vves_n^{im}}{V_n^{tis}}; \quad (3)$$

The $EVD_n^{mat}$ and $EVD_n^{im}$ are the relation of volume of vessels feeding the tissue, to a number of living tissue cells. The amount of immature vessels at a moment "n" depends on an amount of both immature and mature vessels at the previous moment "n−1".

All above described processes have an effect on the changes of the amount of vessels. The volume of immature vessels ($Vves_n^{im}$) (block 1.4) at the moment "n" is a function of the volumes of immature and mature vessels at the moment "n−1". This function has 5 terms, corresponding to the five exponential terms below. They are computed in blocks 1.5, 1.6, 1.7, 1.8 and 1.9.

$$Vves_n^{im} = Vves_{n-1}^{im} * e^{\left(A_{n-1}^{im \Rightarrow new}\frac{T_0}{T_3} - A_{n-1}^{im \Rightarrow reg}\frac{T_0}{T_4} - A_{n-1}^{im \Rightarrow mat}\frac{T_0}{T_6}\right)*\varphi} + Vves_{n-1}^{mat} * \left(e^{\left(A_{n-1}^{mat \Rightarrow new}\frac{T_0}{T_5} + A_{n-1}^{mat \Rightarrow im}\frac{T_0}{T_7}\right)*\varphi} - 1\right); \quad (4)$$

The generation of immature vessels by immature vessels ($A^{im \Rightarrow new}$) is accounted for by block 1.5. The generation of immature vessels by mature vessels ($A^{mat \Rightarrow new}$) is accounted for by block 1.6. The destabilization of mature vessels ($A^{mat \Rightarrow im}$) is accounted for by block 1.7. The maturation of immature vessels ($A^{im \Rightarrow mat}$) is accounted for by block 1.8. The degeneration of immature vessels ($A^{im \Rightarrow reg}$) by is accounted for by block 1.9.

The volume of mature vessels ($Vves_n^{mat}$) (block 1.10) at the moment "n" is also a function of the volumes of immature and mature vessels at the moment "n−1". This function has 2 terms corresponding to the two exponential terms as shown below. They are calculated in blocks 1.7 and 1.9 respectively.

$$Vves_n^{mat} = Vves_{n-1}^{im} * \left(e^{A_{n-1}^{im \Rightarrow mat}\frac{T_0}{T_6}*\varphi} - 1\right) + Vves_{n-1}^{mat}\left(2 - e^{A_{n-1}^{mat \Rightarrow im}\frac{T_0}{T_7}*\varphi}\right) \quad (5)$$

The maturation of immature vessels ($A^{im \Rightarrow mat}$) is accounted for by block 1.7 and the destabilization of mature vessels ($A^{mat \Rightarrow im}$) is accounted for by block 1.9.

Every sub process described in equations (4) and (5) has its characteristic time, denoted by $T_1$ to $T_7$. Resolution is denoted by $T_0$ (the period between "n" and "n−1"). Factor $\phi = \ln 2$ and represents a factor of the conformity.

The terms in eqns. (4) and (5) are functions of the following concentrations: the generation of immature vessels is a function of the concentration of VEGF with the coefficient $\lambda_{im}^{ec}$, $\lambda_{mat}^{ec}$, $\mu_{ec}$ and $\rho_{ec}^{im}$ and Eqns. (6) and (7);

$$\begin{cases} A_{n-1}^{im \Rightarrow new} = \rho_{ec}^{im} * \left(\lambda_{im}^{ec} * \frac{VEGF_{n-1}}{VEGF_{thr}} - \mu_{ec}\Big/\frac{VEGF_{n-1}}{VEGF_{thr}}\right) \\ A_{n-1}^{im \Rightarrow new} = 0 \text{ IF } \left(\lambda_{im}^{ec} * \frac{VEGF_{n-1}}{VEGF_{thr}} - \mu_{ec}\Big/\frac{VEGF_{n-1}}{VEGF_{thr}}\right) \leq 0 \\ A_{n-1}^{im \Rightarrow new} = \rho_{ec}^{im} \text{ IF } \left(\lambda_{im}^{ec} * \frac{VEGF_{n-1}}{VEGF_{thr}} - \mu_{ec}\Big/\frac{VEGF_{n-1}}{VEGF_{thr}}\right) \geq 1 \end{cases} \quad (6)$$

The degeneration of mature vessels is also a function of the concentration of VEGF, level $VEGF_{thr}$, with the coefficient $\mu_{im}$.

$$\begin{cases} A_{n-1}^{mat \Rightarrow new} = \rho_{ec}^{im} * \left(\lambda_{mat}^{ec} * \frac{VEGF_{n-1}}{VEGF_{thr}} - \mu_{ec}\Big/\frac{VEGF_{n-1}}{VEGF_{thr}}\right) \\ A_{n-1}^{mat \Rightarrow new} = 0 \text{ IF } \left(\lambda_{mat}^{ec} * \frac{VEGF_{n-1}}{VEGF_{thr}} - \mu_{ec}\Big/\frac{VEGF_{n-1}}{VEGF_{thr}}\right) \leq 0 \\ A_{n-1}^{mat \Rightarrow new} = \rho_{ec}^{im} \text{ IF } \left(\lambda_{mat}^{ec} * \frac{VEGF_{n-1}}{VEGF_{thr}} - \mu_{ec}\Big/\frac{VEGF_{n-1}}{VEGF_{thr}}\right) \geq 1 \end{cases} \quad (7)$$

The destabilization of mature vessels (block 1.9) is a function of the ratio between Ang1 and Ang2 with the coefficient $\mu_{mat}^{im}$, Eqn. (8-9).

$$A_{n-1}^{im \Rightarrow reg} = \mu_{im}\Big/\frac{VEGF_{n-1}}{VEGF_{thr}}; \quad (8)$$

$$A_{n-1}^{mat \Rightarrow im} = \mu_{mat}^{im}\Big/\frac{AngI_{n-1}}{Ang2_{n-1}}; \quad (9)$$

The maturation of immature vessels (block 1.7) is a more complicated function, Eq. (10).

$$A_{n-1}^{im \Rightarrow mat} = \lambda_{im}^{mat} * \frac{AngI_{n-1}}{Ang2_{n-1}} * \left(\frac{Nper_{n-1}}{\rho_{mat}^{per}}\right)\Big/V_{n-1}^{im}; \quad (10)$$

Maturation in a given moment is a function of a ratio of Ang1/Ang2 at the same moment, with the coefficient $\lambda_{im}^{mat}$. Maturation is also a function of the volume of immature vessels and of the number of free pericytes. The term ($N^{per}/\rho_{mat}^{per})/V^{im}$ gives the fraction of immature vessels can potentially mature (If $(N_{per}/\rho_{mat}^{per})/V^{im} >= 1$ then all immature vessels can mature).

Equ. 11 shows the functional dependence VEGF from EVD with characteristic time $T_8$ and $T_{n-1}^{VEGF}$.

$$VEGF_{n-1} = \quad (11)$$
$$V_{n-1}^{tis} * \lambda_{EVD}^{VEGF}(EVD_{ss} - EVD_{n-2}) * \frac{T_0}{T_8} + VEGF_{n-2} * e^{\left(-\varphi * \frac{T_0}{T_{n-1}^{VEGF}}\right)}$$

IF $VEGF_{n-1} > VEGF_{max}$ THEN $VEGF_{n-1} = VEGF_{max}$
IF $VEGF_{n-1} < VEGF_{en}$ THEN $VEGF_{n-1} = VEGF_{en}$
The initial level $VEGF_{ss}$ characterizes the amount of VEGF secreted when effective tissue vessel density is $EVD_{ss}$.
In a similar way we obtain the dependence of PDGF (12).

$$PDGF_{n-1} = \quad (12)$$

-continued $$V_{n-1}^{tis} * \lambda_{EVD}^{PDGF}(EVD_{ss} - EVD_{n-2}) * \frac{T_0}{T_{14}} + PDGF_{n-2} * e^{\left(-\varphi * \frac{T_0}{T_{h-1}^{PDGF}}\right)}$$

IF $PDGF_{n-1} > PDGF_{max}$ THEN $PDGF_{n-1} = PDGF_{max}$
IF $PDGF_{n-1} < PDGF_{en}$ THEN $PDGF_{n-1} = PDGF_{en}$ The characteristic time $T_{14}$ and $T_{n-1}^{PDGF}$. The above equations 11 and 12 are involved in blocks marked 1.11 & 1.12.

$$Ang2_{n-1} = \qquad (13)$$
$$((Ang2_{en}^{ec} + Ang2_{ss}^{ec}) * EC_{n-2} + Ang2_{ed}^{ec} * (EVD_{ss} - EVD_{n-2}) *$$
$$EC_{n-2}) * \frac{T_0}{T_{10}} + + ((Ang2_{en}^{tc} + Ang2_{ss}^{tc}) * V_{n-2}^{tis} +$$
$$Ang2_{ed}^{tc} * (EVD_{ss} - EVD_{n-2}) * V_{n-2}^{tis}) *$$
$$\frac{T_0}{T_{15}} + Ang2_{n-2} * e^{\left(-\varphi * \frac{T_0}{T_{n-1}^{Ang2}}\right)}$$

In Eqn. (13, 15) Ang2 and Ang1 also depends on the numbers of endothelial cells in immature vessels, which is determined by the Enq. (12), and the numbers of tissue cells $Ang2_{en}^{ec}$, $Ang2_{ss}^{ec}$, $An2_{ed}^{ec}$, $Ang2_{en}^{tc}$, $Ang2_{ss}^{tc}$, $Ang2_{ed}^{tc}$, $T_{n-1}^{Ang2}$, $\rho_{V^{im}}^{ec}$, $Ang1_{en}^{ec}$, $Ang1_{ss}^{ec}$, $Ang1_{ed}^{ec}$, $An1_{en}^{tc}$, $Ang1_{ss}^{tc}$, $Ang1_{ed}^{tc}$, $T_{n-1}^{Ang1}$. The Ang1 induction and Ang2 induction are factors in bocks 1.4, 1.14 and 1.15.

$$EC_{n-1} = \rho_{Vves^{im}}^{ec} * Vves_{n-1}^{im} \qquad (14)$$

The characteristic reaction time for Ang2 generation is $T_{10}$ and $T_{15}$, (13), for Ang1 generation it is $T_9$ and $T_{11}$ (15).

$$Ang1_{n-1} = \qquad (15)$$
$$((Ang1_{en}^{tc} + Ang1_{ss}^{tc}) * V_{n-2}^{tis} + Ang1_{ed}^{tc} * (EVD_{ss} - EVD_{n-2}) * V_{n-2}^{tis}) *$$
$$\frac{T_0}{T_9} + + ((Ang1_{en}^{ec} + Ang1_{ss}^{ec}) * EC_{n-2} + Ang1_{ed}^{ec} *$$
$$(EVD_{ss} - EVD_{n-2}) * EC_{n-2}) * \frac{T_0}{T_{11}} + Ang1_{n-2} * e^{\left(-\varphi * \frac{T_0}{T_{n-1}^{Ang1}}\right)}$$

The addition of free pericytes (block 1.17) at any given moment depends on the level of PDGF at the previous moment, the replication of free pericytes, and on the number of free pericytes released from mature vessels (16). Accordingly, these two processes have the coefficients $\lambda_{bou}^{per}$ and $\lambda_{fr}^{per}$. It is also necessary to take into account the characteristic reaction time of these processes $T_{12}$ and $T_{13}$.

$$Nper_{n-1} = PDGF_{n-2} * \left(\lambda_{bou}^{per} * Vves_{n-2}^{mat} * \frac{T_0}{T_{12}} + \right. \qquad (16)$$
$$\left. \left(Nper_{n-2} - \rho_{mat}^{per} * (Vves_{n-1}^{mat} - Vves_{n-2}^{mat})\right) * \lambda_{fr}^{per} * \frac{T_0}{T_{13}}\right)$$

The number of tissue cells (block 1.18) in the moment, n, depends on their number in the previous moment multiplied by a factor describing the process of cell proliferation and death, $r_{n-1}$.

$$V_n^{tis} = V_{n-1}^{tis} * e^{r_{n-1} * \phi} \qquad (17)$$

$r_{n-1}$ depends on the mitotic index $M_I$ (mitotic time being $T_1$ apoptotic index $A_I$ (apoptotic time being $T_2$), rate of tissue cell growth A and the rate of the death of tumor cells, $\mu$. The two terms in the equation below are involved in blocks 1.191 and 1.121 respectively. Clearly, they are also factors in blocks 1.192 and 1.122 as well as 1.193 and 1.123.

$$r_{n-1} = (M_I + \lambda_{n-1} - \varepsilon_1) * \frac{T_0}{T_1} - (A_I + \mu_{n-1} + \varepsilon_2) * \frac{T_0}{T_2} \text{ where } \varepsilon_1 = \qquad (18)$$
$$\frac{3M_I - 1}{2} \text{ and } \varepsilon_2 = \frac{-\varepsilon_1 A_I}{M_I}$$

The proliferation rate $\lambda$ and the death rate $\mu$ are assumed to be standard sigmoids.

Hence we obtain $\lambda$ and $\mu$ as follows:

$$\mu_{n-1} = 1 - A_I - \frac{(1+\varepsilon_2) * EVD_{n-1}^{\frac{1+\varepsilon_2}{2*A_I - 1+\varepsilon_2}}}{EVD_{n-1}^{\frac{1+\varepsilon_2}{2*A_I - 1+\varepsilon_1}} + \left(\frac{A_I + \varepsilon_2}{1 - A_I} * EVD_{ss}^{\frac{1+\varepsilon_2}{2*A_I - 1+\varepsilon_1}}\right)} \qquad (19)$$

$$\lambda_{n-1} = \frac{(1+\varepsilon_1) * EVD_{n-1}^{\frac{1+\varepsilon_1}{1-2*M_I+\varepsilon_1}}}{EVD_{n-1}^{\frac{1+\varepsilon_1}{1-2*M_I+\varepsilon_1}} + \left(\frac{1 - M_I + \varepsilon_1}{M_I} * EVD_{ss}^{\frac{1+\varepsilon_1}{1-2*M_I+\varepsilon_1}}\right)} - M_I \qquad (20)$$

IV. C. Tissue Control by Pro and Anti Angiogenic Drugs.

Possible drug effects on the pro and anti angiogenesis process indicated in FIG. 2. Note that the blocks in FIG. 2 are identical to those in FIG. 1, except for the additional drug effects shown. The drug effects on the overall process are analyzed by setting the selected drug schedule (number of doses, the dose and the dosing interval). For example the analysis of anti-VEGF drug activity shows that a drug which inhibits VEGF has an optimal efficacy when given by certain treatment protocol. Increasing the administered dose above the optimum can bring about the undesired effect of tissue proliferation, as shown in FIG. 3. In addition, the technique enables one to predict the effects of various drug combinations, for example as shown in FIG. 4.

Other modifications and variations to the invention will be apparent to those skilled in the art from the foregoing disclosure and teachings. Thus, while only certain embodiments of the invention have been specifically described herein, it will be apparent that numerous modifications may be made thereto without departing from the spirit and scope of the invention.

What is claimed is:

1. A computer-implemented method for determining an optimal treatment protocol for a disease related to angiogenesis, comprising:
   creating an angiogenesis mathematical model including biological and mathematical parameters and pro-angiogenic and anti-angiogenic components;
   incorporating effective vessel density (EVD) for regulating switching on and switching off of at least one component in the angiogenesis model;
   incorporating effects of vasculature maturation and mature vessels destabilization;
   selecting pro-angiogenic and anti-angiogenic components, which can influence changes in state of a tissue;
   incorporating effects of drugs in said pro-angiogenic and anti-angiogenic components;

generating a plurality of treatment protocols in a protocol space; and selecting a best treatment protocol based on a pre-determined criteria.

2. The method of claim 1, wherein the model comprises a tissue volume model, an immature vessel model and a mature vessel model.

3. The method of claim 1, wherein steps to regulate dynamics which influences EVD are incorporated.

4. The method of claim 1, wherein the model simultaneously accounts for tissue cell proliferation, tissue cell death, endothelial cell proliferation, endothelial cell death, immature vessel formation and immature vessel regression, immature vessel maturation and mature vessel destabilization.

5. The method of claim 1, wherein the model incorporates temporal parameters that characterize response rate of at least one element associated with angiogenesis.

6. The method of claim 3, wherein EVD is calculated by combining immature vessel density and mature vessel density.

7. The method of claim 1, wherein parameters incorporated into the model comprises tissue volume, number of free endothelial cells, number of free pericytes, volume of mature vessels, volume of immature vessels and concentration of regulator factors.

8. The method of claim 7, wherein the regulatory factors comprise vascular endothelial growth factor (VEGF), platelet derived growth factor (PDGF), angiopoietin 1 (Ang1) and angiopoietin 2 (Ang2).

9. The method of claim 3, wherein EVD is a function of a duration of insufficient perfusion and vice versa.

10. The method of claim 8 wherein the model incorporates threshold levels of regulatory factors and parameter ratios.

11. The method of claim 10, wherein the threshold level is at least one of:
a) VEGF concentration below which no endothelial cells proliferation takes place (A);
b) minimum number of receptors for VEGF above which endothelial cells proliferation takes place (B);
c) VEGF concentration below which endothelial cells, both in the free state as well as when incorporated into immature blood vessels, are subject to apoptosis $VEGF_{thr}$;
d) the minimal number of free pericytes which stimulates the onset of maturation of immature vessels (C);
e) Ang 1/Ang 2 ratio below which mature vessels are destabilized, and above which maturation of immature vessels is enabled (K);
f) EVD value that influences the rate of cell proliferation; and
g) $EVD_{ss}$ value for which the system is in steady state.

12. The method of claim 11 wherein the tissue volume model calculates the tissue volume by a process comprising:
i) comparing EVD against an—$EVD_{ss}$;
ii) if EVD is equal to $EVD_{ss}$ then using a programmed tissue cell proliferation and a programmed tissue cell death (apoptosis) to compute tissue volume;
iii) if EVD>$EVD_{ss}$ then using increased tissue proliferation and decreased tissue cell death to compute tissue volume; and
iv) if EVD<$EVD_{ss}$ then using decreased tissue proliferation and increased tissue cell death to compute tissue volume.

13. The method of claim 12, wherein Ang1 and Ang2 induction are incorporated into steps ii, iii and iv prior to compute tissue volume.

14. The method of claim 13 wherein effects of drugs affecting Ang1 and Ang2 are considered in computing tissue volume.

15. The method of claim 11 wherein the immature vessel model calculates the immature vessels by a process comprising:
i) comparing EVD against an $EVD_{ss}$;
ii) if EVD is equal to $EVD_{ss}$ then setting VEGF to a $VEGF_{ss}$ and PDGF to a $PDGF_{ss}$;
iii) if EVD>$EVD_{ss}$ then using decreased VEGF and decreased PDGF; and
iv) if EVD<$EVD_{ss}$ then using increased VEGF and increased PDGF;
v) comparing VEGF against A;
vi) factoring endothelial cell proliferation if VEGF>A;
vii) comparing VEGF against a VEGF threshold;
viii) factoring free endothelial cell deaths if VEGF>VEGF threshold;
ix) comparing VEGF receptor number against B;
x) if VEGF receptor number is less than B in step ix then considering no angiogenisis prior to computing immature vessel regression;
xi) if VEGF receptor number is not less than B in step ix then computing growth of immature vessels;
xii) if VEGF<A then considering no angiogenesis and computing immature vessel regression;
xiii) computing immature vessels based on growth immature vessels, immature vessel regression and mature vessel destabilization.

16. The method of claim 15, wherein immature vessels computation considers no maturation if Ang2/Ang1<K or if number of free pericytes<C.

17. The method of claim 15, wherein mature vessel destabilization considers ang1/Tie2 interaction blocking.

18. The method of claim 17, wherein no destabilization occurs if Ang2/Ang1>K.

19. The method of claim 15, wherein mature vessel model is computed using a procedure comprising:
i) computing immature vessels;
ii) determining if Ang1/Ang2>K;
iii) determining if number of free pericytes<C;
iv) considering immature vessel maturation if both steps ii and iii are false; and
v) factoring no destablization if step ii is false.

20. The method of claim 15 wherein effects of a drug affecting EC proliferation are factored in computing immature vessels.

21. The method of claim 15 wherein effects of a drug affecting VEGF receptors are factored in computing immature vessels.

22. The method of claim 16 wherein effects of a drug affecting pericyte proliferation are factored in computing immature vessel computation.

23. The method of claim 15 wherein effects of a drug affecting VEGF are factored in computing immature vessels.

24. The method of claim 15 wherein effects of a drug affecting PEGF are factored in computing immature vessel computation.

25. The method of claim 15 wherein effects of a drug affecting Ang1 are factored in computing immature vessels.

26. The method of claim 15 wherein effects of a drug affecting Ang2 are factored in computing immature vessel computation.

27. The method of claim 4, wherein model takes into account duration of a tissue cell proliferation, tissue cell death, endothelial cell proliferation, endothelial cell death, pericytes proliferation, immature vessel regression, immature vessel maturation and mature vessel destabilization.

28. The method of claim 7, wherein model takes into account the duration of VEGF induction, PDGF induction, Ang1 and Ang2 induction by tissue cells and Ang1 and Ang2 induction by endothelial cells.

29. A system for determining an optimal treatment protocol for a disease related to angiogenesis, comprising:
   an angiogenesis mathematical model including biological and mathematical parameters and pro-angiogenic and anti-angiogenic components;
   a treatment protocol space generator that generates a protocol space of possible treatments for the disease;
   a treatment selector that selects an optimal protocol,
   wherein effective vessel density (EVD) regulates switching on and switching off of at least one component in the angiogenesis model;
   wherein the model incorporates effects of vasculature maturation and mature vessels destabilization;
   wherein the system is adapted to affect selection of a subset of the pro-angiogenic and anti angiogenic components which can influence changes in state of a tissue and incorporating effects of drugs in the subset of the pro-angiogenic and anti angiogenic components.

30. The system of claim 29, wherein the model comprises a tissue volume model, an immature vessel model and a mature vessel model.

31. The system of claim 29, wherein steps to regulate dynamics which influences EVD are incorporated.

32. The system of claim 29, wherein the model simultaneously accounts for tissue cell proliferation, tissue cell death, endothelial cell proliferation, endothelial cell death, immature vessel formation and immature vessel regression.

33. The system of claim 29, wherein the model incorporates temporal parameters that characterize response rate of at least one element associated with angiogenesis.

34. The system of claim 31, wherein EVD is calculated by combining immature vessel density and mature vessel density.

35. The system of claim 29, wherein parameters incorporated into the mode comprises tissue volume, number of free endothelial cells, number of free periciytes, volume of mature vessels, volume of immature vessels and concentration of regulator factors.

36. The system of claim 35, wherein the regulatory factors comprise vascular endothelial growth factor (VEGF), platelet derived growth factor (PDGF), angiopoietin 1 (Ang1) and angiopoietin 2 (Ang2).

37. The system of claim 31, wherein EVD is a function of a duration of insufficient perfusion and vice versa.

38. The system of claim 36 wherein the model incorporates threshold levels of regulatory factors and parameter ratios.

39. The system of claim 38, wherein the threshold level is at least one of:
   a) VEGF concentration below which no endothelial cells proliferation takes place (A);
   b) minimum number of receptors for VEGF above which endothelial cells proliferation takes place (B);
   c) VEGF concentration below which endothelial cells, both in the free state as well as when incorporated into immature blood vessels, are subject to apoptosis $VEGF_{thr}$;
   d) the minimal number of free pericytes which stimulates the onset of maturation of immature vessels (C);
   e) Ang 1/Ang 2 ratio below which mature vessels are destabilized, and above which maturation of immature vessels is enabled (K);
   f) EVD value that influences the rate of cell proliferation; and
   g) $EVDS_{ss}$ value for which the system is in steady state.

40. A computer program product, including computer-readable media comprising instructions to implement procedures for determining an optimal treatment protocol for a disease related to angiogenesis, said procedure comprising:
   creating an angiogenesis mathematical model including biological and mathematical parameters and pro-angiogenic and anti-angiogenic components;
   incorporating effective vessel density (EVD) for regulating switching on and switching off of at least one component in the angiogenesis model;
   incorporating effects of vasculature maturation and mature vessels destabilization;
   selecting a subset of the pro-angiogenic and anti-angiogenic components, which can influence changes in state of a tissue;
   incorporating effects of drugs in said subset of the pro-angiogenic and anti-angiogenic components;
   generating a plurality of treatment protocols space; and
   selecting a best treatment protocol based on a pre-determined criteria.

* * * * *